United States Patent [19]

Vahlne et al.

[11] Patent Number: 5,627,035
[45] Date of Patent: May 6, 1997

[54] PEPTIDES THAT BLOCK HUMAN IMMUNODEFICIENCY VIRUS AND METHODS OF USE THEREOF

[75] Inventors: Anders Vahlne, Hovås; Bo Svennerholm, Göteborg; Lars Rymo, Hovås; Peter Horal; Stig Jeansson, both of Göteborg, all of Sweden

[73] Assignee: Syntello Vaccine Development AB, Goteborg, Sweden

[21] Appl. No.: 494,763

[22] Filed: Jun. 26, 1995

Related U.S. Application Data

[63] Continuation of Ser. No. 988,127, Feb. 12, 1993, which is a continuation-in-part of Ser. No. 571,080, filed as PCT/SE91/00544 published as WO92/03147 Mar. 5, 1992, abandoned.

[51] Int. Cl.$^6$ .......................... G01N 33/53; A61K 39/21; C07K 5/00; C07K 16/00
[52] U.S. Cl. .......................... 435/7.2; 530/327; 530/328; 530/329; 530/330; 424/188.1
[58] Field of Search .......................... 530/328, 327; 435/7.2; 424/188.1

[56] References Cited

U.S. PATENT DOCUMENTS

| | | |
|---|---|---|
| 4,612,337 | 9/1986 | Fox et al. |
| 4,818,540 | 4/1989 | Chien et al. |
| 5,126,399 | 6/1992 | Arlinghaus et al. .......... 525/54.1 |

FOREIGN PATENT DOCUMENTS

| | | | |
|---|---|---|---|
| 0267802 | 5/1988 | European Pat. Off. ..... | G01N 33/569 |
| 0339504 | 4/1989 | European Pat. Off. | |
| 8702775 | 5/1987 | WIPO | |
| 8903391 | 4/1989 | WIPO | |

OTHER PUBLICATIONS

Goudsmit, et al, 1988, "Human Immunodeficiency Virus type 1 . . ." PNAS 85: 4478–4482.
Chemical Abstract 99:187072 (1983).
Chemical Abstract 101:204450k (1984).
Chemical Abstract 102:43238a (1985).
Chemical Abstract 96:85988h (1982).
Javaherian, et al, 1989, "Principal Neutralizing domain . . ." PNAS 86: 6768–6772.
Sandstrom, et al, 1987, "Antiviral therapy in AIDS . . ." Drugs 34: 372–390.
Martin, "Fast-Acting Slow Viruses", Nature, 345:572–573 (1990).
Smith et al., "Blocking of HIV-1 Infectivity by a Soluble Secreted Form of the CD4 Antigen", Science, 238:1704–1706.
Weber, "Blocks on the Viral Exit", Nature, 345:573–574 (1990).
Richards, "Inhibition of the Aspartic Proteinase from HIV-2", FEBS Lett. 253:214–216 (1989).
Meek et al., "Inhibition of HIV-1 Protease in Infected T-Lympho-cytes by Synthetic Peptide Analogues", Nature, 343:90–92 (1990).
Miller et al., "Antiviral Activity of Carbobenzoxy Di- and Tri-peptides on Measles Virus", Appl. Microbiol., 16:1489–1496 (1968).
Nicolaides et al., "Potential Antiviral Agents, Carbobenzoxy Di- and Tripeptides Active Against Measles and Herpes Viruses", J. Med. Chem., 11:74–79 (1968).
Finberg et al., "Prevention of HIV-1 Infection and Preservation of CD4 Function by the Binding of CPF's to gp120", Science, 249:287–291 (1990).
Erickson & Merrifield, "Solid Phase Peptide Synthesis", in: The Proteins, 3rd Ed. (1976), vol. 2, Academic Press, N.Y., Chap. 3.
Bergot et al., "Utility of Trifluoromethane Sulfonic Acid as a Cleavage Reagent in Solid Phase Peptide Synthesis", Applied Bio-systems User Bulletin, Peptide Synthesizer, Issue No. 16., Sep. 2, 1986.
Jeansson et al., "Elimination of Mycoplasmas From Cell Cultures Utilizing Hyperimmune Sera", Experimental Cell Research, 161: 181–188 (1985). Sep. 2, 1986.
"Proceedings of a Symposium on Acylovor", The Amer. Journal of Medicine, Jul. 20, 1982.
Erickson et al., "Design, Activity, and 2.8Å Crystal Structure of a $C_2$ Symmetric Inhibitor Complexed to HIV-1 Protease", Science, 249:527–533 (1990).
Moore et al., "In vivo Depression of Lymphocyte Traffic in Sheep by VIP and HIV (AIDS)-Related Peptides", Immunopharmacol., 16:181–189 (1988).
Rydon et al., "Polypeptides. Part IV. The Self-condensation of the Esters of Some Peptides of Glycine and Proline"; Journal of Chemical Society, Part IV; pp. 3642–3650, (1956).
Holley et al., "Prediction of optimal peptide mixtures to induce broadly neutralizing antibodies to human immunodeficiency virus type 1"; Proc. Nat'l. Acad. Sci.; vol. 88; pp. 6800–6804; (1991).

*Primary Examiner*—Lynette F. Smith
*Attorney, Agent, or Firm*—Knobbe, Martens, Olson & Bear

[57] ABSTRACT

It has now been found that relatively short peptides such as the tripeptide glycyl-prolyl-glycine are able to effectively inhibit HIV infection of cells and syncytia formation between HIV infected and and non-infected cells. The peptides are suitable for therapy of patients infected with HIV and in prevention of HIV infection.

7 Claims, 6 Drawing Sheets

AZT

PEPTIDES THAT BLOCK HUMAN IMMUNODEFICIENCY VIRUS AND METHODS OF USE THEREOF

This application is a continuation application of U.S. patent application No. 07/988,127, filed Feb. 12, 1993, now abandoned which is a continuation-in-part of U.S. patent application 07/571,080, filed as PCT/SE91/00544 Aug. 20, 1991, published as WO92/03147 Mar. 5, 1992, now abandoned.

This invention relates to peptides which inhibit human immunodeficiency virus (HIV) infection and HIV induced syncytia formation between cells. The peptides are useful in therapy and prevention of HIV infection.

BACKGROUND OF THE INVENTION

HIV-1 is the name given to a group of highly related viruses which have been identified as the primary etiologic agent of the acquired immunodeficiency syndrome (AIDS) and AIDS related condition (ARC) in humans. HIV-1, also known as HTLV-III, LAV and ARV, is a major worldwide health problem.

HIV is a relatively complex retrovirus containing at least seven genes. The viral structural genes designated gag, pol and env respectively code for the viral core proteins, reverse transcriptase, and the viral glycoproteins of the viral envelope. The other HIV genes are accessory genes involved in vital replication. The gag and env genes encode polyproteins, i.e., the proteins synthesized from each of these genes are post-translationally cleaved into several smaller proteins. Previous studies have shown that the proteins coded by the gag and especially the env regions of the HIV genome are immunologically important, since antibodies to the products of the gag and env genes are found in the sera of patients infected with HIV.

The env gene encodes a glycoprotein (gp160) with an apparent molecular weight (Mw) of about 160,000 Daltons which is post-translationally cleaved into two glycoproteins, gp120 and gp41, of Mw 120,000 and 41,000 Daltons, respectively. Glycoprotein gp120 is the external protein of the viral envelope, while gp41 is a transmembrane protein. The gp120 protein associates noncovalently with gp41 such that gp120 is exposed on the cell surface. Both gp120 and gp41 are immunogenic, with antibodies to the proteins readily detectable in sera obtained from patients infected with HIV but who are asymptomatic, and ARC and AIDS patients.

The HIV coat protein gp120 binds to the T cell surface protein CD4, also known as the HIV receptor protein. The gp120 protein is crucial to HIV infection, because gp120 binds to CD4 with high affinity to effect HIV entry into the cell. Cells infected by HIV express a cell surface form of gp120 and also shed a soluble form of gp120 protein from their surface. This extracellular, soluble gp120 binds to CD4 on uninfected cells with high affinity and appears to induce cell death by an unknown mechanism. It is characteristic of HIV infection that infected cells may not lyse, consequently cells expressing gp120 may survive for extended periods of time, acting as reservoirs of the virus and gp120.

HIV infection is largely dependent on gp120 binding to CD4 as underscored by the finding that soluble recombinant CD4 lacking its transmembrane and cytosolic sequences can block HIV infectivity and soluble gp120 mediated cell killing. The soluble CD4 also binds to HIV infected cells and soluble gp120. Smith et al., "Blocking of HIV-1 Infectivity by a Soluble, Secreted Form of the CD4 Antigen", Science, 238: 1704–1706 (1987). The use of soluble CD4 as a therapeutic agent is expensive, however, and there are problems with delivery and stability. Furthermore, CD4 treatment can result in the formation of antibodies specific to CD4 with subsequent autoimmune disease. Weber, "Blocks on the Viral Exit", Nature, 345: 573–574 (1990).

HIV infection is also thought to occur by cell-to-cell transmission. This form of infection does not rely on extracellular HIV binding to CD4, and cannot be prevented by agents such as soluble CD4. In order to effect cell-to-cell transmission, an infected cell forms contacts termed syncytia with a non-infected cell thus enabling direct transmission of the virus. Syncytia are visible under a light microscope and are indicators of HIV infection.

Since HIV-1 was first identified as the etiologic agent of AIDS, substantial progress has been made in studies on the virus per se, mechanisms by which the virus causes disease and in the development of diagnostic tests to detect exposure to the virus or infection. Progress in HIV vaccines and therapy has been slow due to the heterogeneous nature of the virus and the lack of suitable animal models. See, e.g., Martin, "Fast-Acting Slow Viruses", Nature, 345: 572–573 (1990).

While a variety of approaches have been taken to formulate pharmaceutical agents suitable for AIDS therapy, many if not all of the drugs create serious side effects which greatly limit their usefulness as therapeutic agents.

One drug target is the HIV protease crucial to virus development. HIV protease is an aspattic protease and hence can be inhibited by agents such as H-261 (tBoc-His-Pro-Phe-His-Leuψ[CHOH-CH$_2$]Val-Ile-His) (Seq. I.D. No. 2) and acetyl-pepstatin. Richards, "Inhibition of the Aspattic Proteinase from HIV-2", FEBS Lett., 253: 214–216 (1989). Unfortunately, inhibitors of aspattic proteases are nonselective and therefore toxic when used in vivo. In addition, several peptide analogues have been found to inhibit HIV protease. Meek et al., "Inhibition of HIV-1 Protease in Infected T-lymphocytes by Synthetic Peptide Analogues", Nature, 343: 90–92 (1990). Recently a two-fold symmetric inhibitor of HIV protease was described. Erickson et al., "Design, Activity, and 2.8 Å Crystal Structure of a C$_2$ Symmetric Inhibitor Complexed to HIV-1 Protease", Science, 249: 527–533 (1990). This symmetric inhibitor has a selective activity against HIV-1 protease, it is about 10,000 fold more potent against HIV-1 protease than against related cellular enzymes.

The HIV reverse transcriptase is likewise necessary for effective HIV infection and thus; drugs are being sought which inhibit the enzyme's activity. Several nucleoside derivatives have been found to inhibit HIV reverse transcriptase. Foremost among these drugs is azidothymidine (AZT, Zidovidine®). AZT causes serious side effects, however, such that many patients cannot tolerate its administration. Other nucleoside analogues that inhibit HIV, reverse transcriptase have been found to cause even more serious side effects then does AZT.

Several agents have been found to inhibit binding of HIV to T cells. For instance, a pentapeptide and an octapeptide derived from vasoactive intestinal peptide (VIP) have been found to inhibit HIV infection. Moore et al., "In vivo Depression of Lymphocyte Traffic in Sheep by VIP and HIV (AIDS)—Related Peptides", Immunopharmacol., 16: 181–189 (1988). Unfortunately, these peptides have the side effect of mimicking the immunosuppression of HIV infection by inhibiting proliferation of T4 cells and are thus useless for therapy.

Recently, N-carbomethoxycarbonyl-prolylphenylalanyl benzyl ester (CPF), a derivative of the dipeptide prolylphenylalanine, was shown to inhibit HIV-1 infection in vitro. CPF interacts with gp120 and blocks the binding of gp120 to CD4. Finberg et al., "Prevention of HIV-1 Infection and Preservation of CD4 Function by the Binding of CPF's to gp120", Science, 249: 287–291 (1990).

Small peptides have been used in the treatment of measles virus and herpes virus infections. A series of carbobenzoxy (Z) peptides, including Z-D-Pro-D-Phe have been shown to inhibit measles and herpes viruses. Miller et al., "Antiviral Activity of Carbobenzoxy Di- and Tripeptides on Measles Virus", Appl. Microbiol., 16: 1489–1496 (1968); and Nicolaides et al. "Potential Antiviral Agents. Carbobenzoxy Di- and Tripeptides Active Against Measles and Herpes Viruses", J. Med. Chem., 11: 74–79 (1968). These compounds interact with the target cell and not with the viral protein.

It would be useful in the therapy and prevention of AIDS to have a specific, selective anti-HIV therapeutic agent that causes few, if any, side effects.

SUMMARY OF THE INVENTION

It has now been found that certain relatively short peptides are able to effectively inhibit HIV infection of host cells and syncytia formation between infected and non-infected cells. The peptides of the invention have in common a carboxy terminal dipeptide portion with the amino acid sequence Pro-Gly (PG). The tripeptide Gly-Pro-Gly (GPG) is the preferred species. This tripeptide may be used itself or may be extended amino terminally to form a tetra-, penta- or hexapeptide. The peptides are suitable for therapy in mammals including man infected with HIV and in prevention of HIV infection.

BRIEF DESCRIPTION OF THE DRAWINGS

FIG. 1 is discussed in Example 5.

FIG. 2 is discussed in Example 5.

FIG. 3 is discussed in Example 8.

DETAILED DESCRIPTION OF THE INVENTION

Figure 1A:
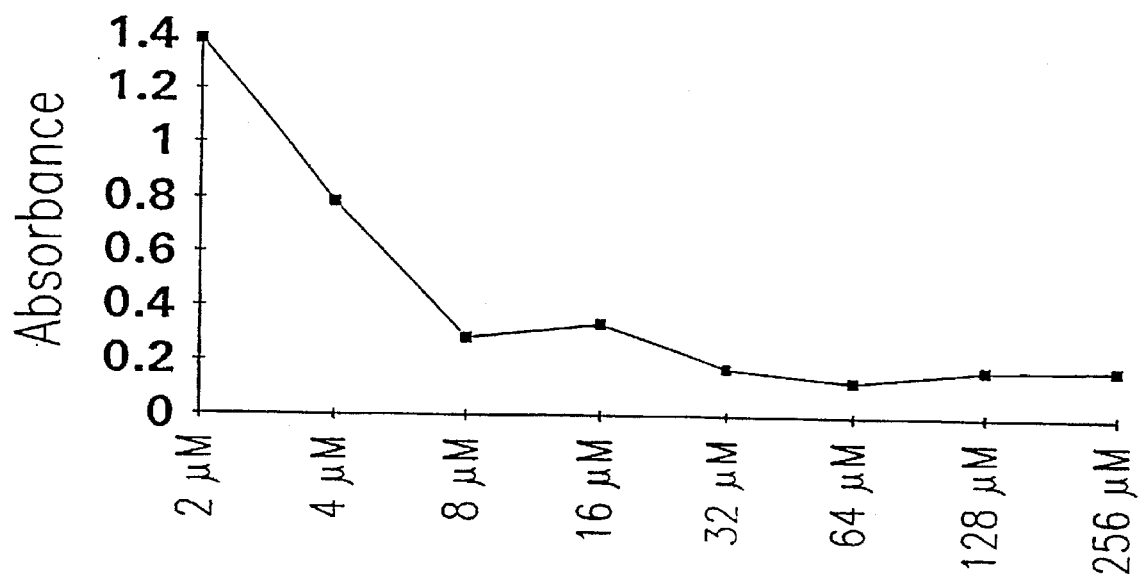
FIG. 1 is a series of graphs (1A–1D) depicting dose response experiments of Gly-Pro-Gly or AZT on HTLV-IIIB replication in H9 cells.

It has now been found that the dipeptide, Pro-Gly and peptides containing the tripeptide amino acid sequence Gly-Pro-Gly prevent both HIV infection and syncytia formation. Such peptides are useful in treatment of HIV infected patients, as preventative agents for patients at-risk of HIV infection and for use in medical devices where the risk of exposure to HIV is significant.

The peptides listed in Table 1 were tested in the course of the research leading to the present invention. These peptides were synthesized according to the method of Erickson and Merrifield, "Solid Phase Peptide Synthesis", in: The Proteins, 3rd Edition (1976), Vol. 2, Academic Press, New York, Chapter 3, but could be synthesized by any method known in the art.

TABLE 1

Amino Acid Sequence of Peptides Tested,

Tyr-Arg-Gly-Pro-Gly (Seq. I.D. No. 2)
Gly-Pro-Gly
Gly-Pro-Gly-Arg (Seq. I.D. No. 3)
Arg-Gly-Pro-Gly (Seq. I.D. No. 4)
Arg-Gly-Pro-Gly-Arg (Seq. I.D. No. 5)
Pro-Gly-Arg
Gly-Pro-Ala
Gly-Pro-Gly-Gly (Seq. I.D. No. 6)
Gly-Gly-Gly
Pro-Gly
Gly-Pro Abbreviations used Tyr—tyrosine Arg—arginine Gly—glycine Pro—proline Ala—alanine The peptides were tested for their ability to inhibit the spread of HIV infection from infected cells to non-infected cells. The spread of infection was determined by monitoring HIV protein p24 production, indicative of viral replication; syncytia formation; and the number of HIV infected cells as determined by indirect immunofluorescence.

It was found that several peptides did inhibit HIV infection while, surprisingly, other virtually identical peptides failed to do so. The results shown in Tables 3 to 6 indicate that the peptides with prolyl-glycine as the carboxy terminal amino acids, Tyr-Arg-Gly-Pro-Gly, (Seq. I.D. No. 2) Gly-Pro-Gly, Arg-Gly-Pro-Gly (Sew. I.D. No. 5) and Pro-Gly, prevent HIV infection as determined by both p24 levels and syncytia formation. Those peptides containing a carboxy terminal arginine residue, Gly-Pro-Gly-Arg, (Seq. I.D. No. 3) Arg-Gly-Pro-Gly-Arg (Seq. I.D. No. 5) and Pro-Gly-Arg, did not prevent HIV infection as determined by the assays. The presence of an arginine residue per se was not the inhibitory factor since peptides with an amino terminal arginine residue and a carboxy terminal glycine residue prevented infection. A further unexpected finding was that the peptide, Gly-Pro-Gly, on a weight basis, was most effective at preventing HIV infection. Peptides lacking the carboxy terminal prolyl-glycine dipeptide (Gly-Pro-Ala, Gly-Pro-Gly-Gly, (Seq. I.D. No. 6) Gly-Gly-Gly and Gly-Pro) do not inhibit HIV infectivity. Thus the carboxy terminal dipeptide prolyl-glycine is essential to the present invention.

The present invention therefore encompasses peptides capable of preventing HIV infection that contain the dipeptide Pro-Gly at the carboxy terminus. The preferred peptide contains only the Gly-Pro-Gly sequence but amino acid residues may be added to the amino terminus of the peptide without significant deleterious effects. For practical purposes the peptides should be less than about six amino acids in length. Longer peptides are less practical since they incur greater expense, may be less efficacious and may generate an immune response. It is preferred that the peptides possess an amido group at their carboxy termini rather than a carboxyl group as it has surprisingly been found that peptides possessing a carboxy terminal carboxyl group are ineffective at preventing HIV infection. The carboxy terminus can also contain any moiety that does not inhibit anti-HIV activity. Unless otherwise indicated, the peptides contain an amido group at their carboxy termini.

The invention thus encompasses peptides of the following molecular formulae:

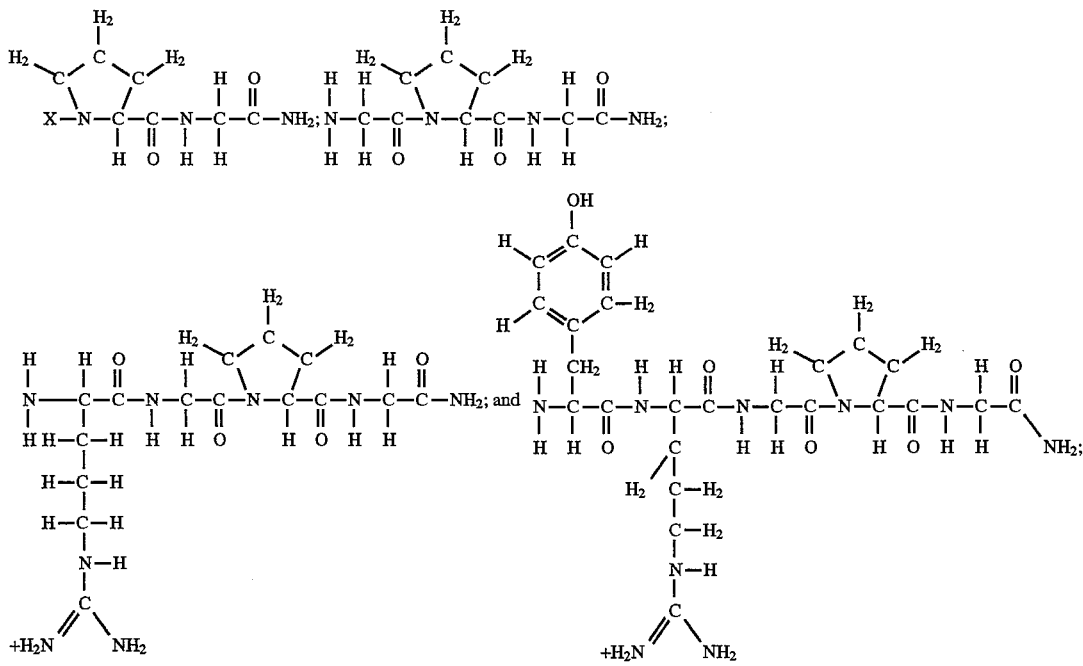

These compounds are represented generically by the formula

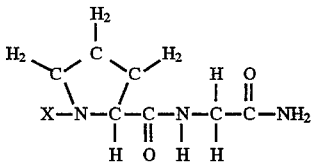

wherein X includes one to 4 additional amino acid residues or analogues of amino acid residues bound via an amide linkage and a hydrogen atom. The additional amino acid residues include but are not limited to glycine, arginyl-glycine and tyrosyl-arginyl-glycine or analogues thereof.

The peptides of the invention are suitable for treatment of subjects either as a preventative measure to avoid HIV infection or as a therapeutic to treat patients already infected with HIV. Although anyone could be treated with the peptides as a preventative measure, the most suitable subjects are people at risk for HIV infection. Such subjects include but are not limited to homosexuals, prostitutes, intravenous drug users, hemophiliacs, children born to HIV infected mothers and those in the medical profession who have contact with patients or biological samples.

It has now been found that, surprisingly, the peptides act synergistically with AZT to reduce infectivity of various HIV isolates. It is thus a preferred embodiment of the present invention that the peptides be given in combination with AZT where AZT is tolerated by the patient. The peptides may well work synergistically with other anti-HIV drugs, combinations of the peptides with such drugs are encompassed by the present invention.

The peptides can be administered alone or in combination with other peptides or with other anti-HIV pharmaceutical agents and can be combined with a physiologically acceptable carrier therefor. The effective amount and method of administration of the particular peptide formulation may vary based on the individual patient and the stage of the disease and other factors evident to one skilled in the art. The route(s) of administration useful in a particular application are apparent to one of skill in the art. Routes of administration include but are not limited to topical, transdermal, parenteral, gastrointestinal, transbronchial and transalveolar. A suitable dosage range is one that provides sufficient peptide to attain a tissue concentration of about 1–10 µM as measured by blood levels. The absolute amount given to each patient depends on pharmacological properties such as bioavailability, clearance rate and route of administration. Higher tissue concentrations can be maintained without harm due to the low toxicity of the peptides.

Routes of administration include, but are not limited to, topical, transdermal, parenteral, gastrointestinal, transbronchial and transalveolar. Topical administration is accomplished via a topically applied cream, gel, rinse, etc. containing a peptide. Transdermal administration is accomplished by application of a cream, rinse, gel, etc. capable of allowing the peptide to penetrate the skin and enter the blood stream. Parenteral routes of administration include but are not limited to electrical or direct injection such as direct injection into a central venous line, intravenous, intramuscular, intraperitoneal or subcutaneous injection. Gastrointestinal routes of administration include but are not limited to ingestion and rectal. Transbronchial and transalveolar routes of administration include but are not limited to inhalation, either via the mouth or intranasally.

The present invention provides compositions of peptide-containing compounds suitable for topical application including but not limited to physiologically acceptable implants, ointments, creams, rinses and gels. Any liquid, gel or solid, pharmaceutically acceptable, base in which the peptides are at least minimally soluble is suitable for topical use in the present invention. Compositions for topical application are particularly useful during sexual intercourse to prevent transmission of HIV. Suitable compositions for such use include but are not limited to vaginal or anal suppositories, creams and douches.

Compositions suitable for transdermal administration include but are not limited to pharmaceutically acceptable suspensions, oils, creams and ointments applied directly to the skin or incorporated into a protective carrier such as a transdermal device (so-called "patch"). Examples of suitable creams, ointments etc. can be found for instance in the Physician's Desk Reference. Examples of suitable transdermal devices are described for instance in U.S. Pat. No. 4,818,540 issued Apr. 4, 1989 to Chien et al.

Compositions suitable for parenteral administration include but are not limited to pharmaceutically acceptable sterile isotonic solutions. Such solutions include but are not limited to saline and phosphate buffered saline for injection into a central venous line, intravenous, intramuscular, intraperitoneal or subcutaneous injection of the peptides.

The present invention includes compositions of the peptides suitable for gastrointestinal administration including, but not limited to pharmaceutically acceptable, powders, pills or liquids for ingestion and suppositories for rectal administration. Due to the most common routes of HIV infection and ease of use, gastrointestinal administration, particularly oral administration, is the preferred embodiment of the present invention. It has previously been shown in other virus-host systems that specific antiviral activity of small peptides can be detected in serum after oral administration. Miller et al., Appl. Microbiol., 16: 1489 (1968). Since small peptides apparently evade degradation by the patient's digestive system they are ideal for oral administration.

The present invention further includes compositions of the peptides suitable for transbronchial and transalveolar administration including but not limited to various types of aerosols for inhalation. For instance, pentamidine is administered intranasally via aerosol to AIDS patients to prevent pneumonia caused by *Pneumocystis carinii*.

The present invention further contemplates devices suitable for transbronchial and transalveolar administration of the peptides. Such devices include but are not limited to, atomizers and vaporizers.

The above-mentioned compositions and methods of administration are meant to describe but not limit the methods of administering the peptide-containing compositions of the invention. The methods of producing the various compositions and devices are within the ability of one skilled in the art and are not described in detail here.

The methods of producing suitable devices for injection, topical application, atomizers and vaporizers are known in the art and will not be described in detail.

The peptides of the present invention are also suitable for use in situations where prevention of HIV infection is important. For instance, medical personnel are constantly exposed to patients who may be HIV positive and whose secretions and body fluids contain the HIV virus. Further, the peptides can be formulated into antiviral compositions for use during sexual intercourse so as to prevent transmission of HIV. Such compositions are known in the art and also described in International Application published under the PCT publication No. WO90/04390 on May 3, 1990 to Modak et al. which is incorporated herein by reference.

The invention further provides a coating for medical equipment such as gloves, sheets and work surfaces which protects against HIV transmission. Alternatively, the peptide(s) can be impregnated into a polymeric medical device. Particularly preferred are coatings for medical gloves. Additionally, coatings for condoms are particularly pertinent considering sexual transmission of HIV.

Coatings suitable for use in medical devices can be provided by a powder containing the peptide(s) or by a polymeric coating into which the peptide(s) is suspended. Suitable polymeric materials for coatings or devices are those which are physiologically acceptable and through which a therapeutically effective amount of the peptide(s) can diffuse. Suitable polymers include but are not limited to polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described for instance in U.S. Pat. No. 4,612,337, issued Sep. 16, 1986 to Fox et al. which is incorporated herein by reference.

The invention further encompasses functionally equivalent variants of the peptides which do not significantly affect the anti-viral properties of the peptides. For instance, various analogues, or peptidomimetics, are known in the art and can be used to replace one or more of the amino acids in the peptides. Analogues are defined as peptides which are functionally equivalent to the peptides of the present invention but which contain certain non-naturally occurring or modified amino acid residues. Additionally, polymers of one or more of the peptides are within the scope of the invention.

The use of peptide analogues can result in peptides with increased activity, that are less sensitive to enzymatic degradation, more capable of penetrating the central nervous system and which are more selective. A suitable proline analog is 2-aminocyclopentane carboxylic acid ($\beta Ac^5c$) which has been shown to increase activity of a native peptide more than 20 times. Mierke et al., "Morphiceptin Analogues Containing 2-aminocyclopentane Carboxylic Acid as a Peptidomimetic for Proline", Int. J. Peptide Protein Res., 35: 35–45 (1990). See also Portoghese et al., "Design of Peptidomimetic S Opioid Receptor Antagonists Using the Message-Address Concept", J. Med. Chem., 33: 1714–1720 (1990); and Goodman et al., "Peptidomimetics: Synthesis, Spectroscopy, and Computer Simulations", Biopolymers, 26: S25–S32 (1987).

One common drawback to previously proposed peptide based vaccines is caused by the heterogeneity of the HIV genome such that immunity to one isolate does not necessarily confer immunity to another isolate. The peptides of the invention overcome this drawback, in that they provide protection against a wide range of HIV isolates. It has now been shown that the peptides of the present invention neutralize not only "street strains" of HIV (those obtained from infected donors) but also simian immunodeficiency virus, rendering the peptides ideal for studying treatment of animal models of HIV infection. The activity of the peptides against a variety of HIV isolates probably occurs due to the fact that the amino acid sequence Gly-Pro-Gly is highly conserved among widely variant HIV isolates. LaRosa et al., "Conserved Sequence and Structural Elements in the HIV-1 Principal Neutralizing Determinant", Science, 249: 932–935 (1990).

The invention is further illustrated by the following specific examples which are not intended in any way to limit the scope of the invention. Note that in the following Tables, the amino acid residues are abbreviated as follows: Gly, G; Pro, P; Arg, R; Tyr, Y; and Ala, A.

EXAMPLE 1

Peptide Synthesis

An Applied Biosystems peptide-synthesizer Model 430 A, was utilized for the synthesis of the peptides of the present invention. Each synthesis used a p-methylbenzylhydrylamine solid phase support resin (Peptides International, Louisville, Ky.). The peptides were synthesized according to the Users Manual for Peptide Synthesizer Model 430A, Applied Biosystems, (1986).

All amino acids for use in synthesis contained t-butylcarbonyl groups (t-Boc) protecting the α-NH$_2$ group and were obtained from Novabiochem AG, Switzerland. Amino acids with reactive side chain groups contained additional protective groups to prevent unwanted and undesirable side chain reactions. The individual protected amino acids used in synthesizing all of the peptides are set forth in Table 2.

TABLE 2

Amino Acids Used in the Synthesis of Peptides

Boc-Arg (Tos)-OH
Boc-Gly-OH
Boc-Pro-OH
Boc-Tyr-(2-Br-Z)-OH
Boc-Ala-OH
Tos=Tosyl or p-Toluene sulfonic acid
2-Br-Z=Carbobenzoxy bromide After completion of a particular synthesis, the protecting groups were removed from the synthesized peptide and the peptide was cleaved from the solid support resin by treatment with trifluoromethane sulfonic acid (TFMSA) according to the method described by Bergot et al., "Utility of Trifluoromethane Sulfonic Acid as a Cleavage Reagent in Solid Phase Peptide Synthesis", Applied Biosystems User Bulletin, Peptide Synthesizer, Issue No. 16, Sep. 2, (1986). The following is the detailed protocol used.

1. For 1 gram peptide-resin, 3 ml thio-anisole 1,2-ethanedithiol (2:1) was added as scavenging agent and the mixture was incubated with continuous stirring for 10 min. at room temperature.
2. Trifluoracetic Acid (TFA), 10 ml, was added and stirred continuously for 10 min. at room temperature.
3. TFMSA, 1 ml, was added dropwise with forceful stirring and reacted for 25 min. at room temperature.
4. Following cleavage, the peptides were precipitated with and washed with anhydrous ether.
5. The precipitated and washed peptides were dissolved in a small volume of TFA.
6. The dissolved peptides were again precipitated and washed as above in step 4 and the precipitate was dried under a stream of N$_2$.

Prior to use in specific assays, the peptides can be further purified, if desired, by reverse phase high performance liquid chromatography (HPLC). A particularly suitable column for such purification is the reverse-phase Vydak® C-18 column using a water (TFA)—acetonitrile (TFA) gradient to elute the peptides.

EXAMPLE 2

Infectivity Assay

Table 1 lists the peptides and their amino acid sequences tested against the following virus/cell systems:

(1) HTLV-111B/H9 Denmark (obtained from Denmark, Bent Faber-Vestergard);

(2) HTLV-111B/H9 New York (obtained from Dr. William Hall, North Shore Hospital, Manhasset, N.Y.); and (3) ELI-1/HUT (obtained from Dr. Levy, San Francisco, Calif.).

Virus at 100 50% tissue culture infectious doses (TCID$_{50}$) and peptides at concentrations of 250 and 25 µg/ml were added to the cells simultaneously and incubated for 2 hours at 4° C. with frequent stirring. Subsequently, the temperature was increased to 37° C. and the mixtures were subjected to a second incubation for 2 hours. Following the second incubation, the cells were centrifuged at 325 x g and washed once in RPMI medium (Gibco Laboratories, N.Y.). Cells, at a concentration of 5×10$^5$/ml, were then added to 24 multidish well plates at a final volume of 1.5 ml of growth medium (RPMI supplemented with 10% fetal calf serum (FCS), antibiotics and polybrene (2 µg/ml)), with the addition of peptides at dilutions of 250 or 25 µg/ml. As controls, cells infected with virus only or virus in the presence of azidothymidine (AZT, Zidovidine®) (at concentrations of 20, 2 and 0.2 µM) were used. As additional controls, two HIV infected cell cultures (designated pos. controls 1 and 2, Tables 3–5) and two uninfected cell cultures (designated neg. controls 1 and 2) were used.

Growth medium, without any additives of peptides or AZT, was changed on days 6 and 10 post-infection (p.i.). Infected cells were continuously monitored for formation of syncytia and the growth medium supernatants were analyzed at days 9–12 p.i. for p24 antigen which is an indicator of HIV replication.

Briefly, the following protocol was used for detection of the p24 antigen. HIV p24 antigen was determined using a rabbit anti-p24 polyclonal antiserum as capture antibody and a biotinylated rabbit anti-p24 polyclonal antibody was used as detecting antibody in an avidin-horse radish peroxidase (HRP) ELISA. The sensitivity of the assay allowed detection of approximately 50 pg of p24 antigen per ml supernatant. The results are presented as absorbance values at 454 nm with higher absorbance indicating higher protein concentration and hence HIV infection. Serial dilutions of the supernatants were made so as to detect p24 concentration in the most accurate range (<2.0 absorbance units).

Note that the cell line ELI1-HUT does not form syncytia upon infection with HIV; syncytia formation was thus not monitored for this cell line. At the end of the experiment, the cells were collected and fixed on slides with acetone according to standard procedures as described in Jeansson et al., Exp. Cell Res., 161: 181–188 (1985). The number of infected cells were then determined by indirect immunofluorescence using a human HIV positive serum diluted 1/100 and FITC conjugated antihuman IgG (Bio Merieux, France) diluted 1/200. The results obtained are shown in Tables 3–6.

The results in Tables 3–5 show that cells infected with HIV and treated with peptides Gly-Pro-Gly-Arg (Seq. I.D. No. 3), Arg-Gly-Pro-Gly-Arg (Seq. I.D. No. 5) and Pro-Gly-Arg or with no drug, became infected. However, HIV infected cells treated with peptides Tyr-Arg-Gly-Pro-Gly, (Seq. I.D. No. 2) Gly-Pro-Gly and Arg-Gly-Pro-Gly or AZT showed a reduced amount of infection as determined by both p24 synthesis and syncytia formation. In fact, the peptide Gly-Pro-Gly at a concentration of 25 µg/ml (corresponding to approximately 100 µM) was only slightly less effective than the highest concentration of AZT tested (20 µM) in preventing both p24 production and syncytia formation.

The efficacies of oligopeptides Gly-Pro-Ala, Gly-Gly-Gly, Gly-Pro-Gly-Gly (Seq. I.D. No. 6) and dipeptides Gly-Pro and Pro-Gly were evaluated as described above using the HTLV-IIIB/H9 N.Y. combination of virus and cells. The results are shown in Table 6. It is evident that the dipeptide Pro-Gly had an inhibitory effect on HIV replication as determined by both p24 synthesis and syncytia formation. The other peptides, Gly-Pro-Ala, Gly-Gly-Gly, Gly-Pro-Gly-Gly (Seq. I.D. No. 6) and Gly-Pro, had no inhibitory effect on HIV replication as shown in Table 6.

In tables 3–6, the p24 content of the supernatants of infected cells was determined by diluting the supernatants of infected cells in serial tenfold dilutions (1/10, 1/100, 1/1000 and 1/10,000) and analyzing in ELISA as described above. Results are indicated by the absorbance values (454nm) of respective dilutions.

TABLE 3

HTLV IIIB-/9 N. Y.

| PEPTIDE | CONC. µg/ml | p24 1/10 | p24 1/100 | p24 1/1,000 | p24 1/10,000 | % OF POS CELLS | # OF SYNCYTIA/WELL Day 9 | # OF SYNCYTIA/WELL Day 14 |
|---|---|---|---|---|---|---|---|---|
| Tyr—Arg—Gly—Pro—Gly(SEQ. I.D. NO.2) | 250 | 0.135 | 0.103 | 0.091 | 0.115 | 0 | 0 | 0 |
|  | 25 | 2.117 | 0.638 | 0.094 | 0.144 | 10 | 11 | >100 |
| Gly—Pro—Gly | 250 | 0.148 | 0.123 | 0.1 | 0.108 | 0 | 0 | 0 |
|  | 25 | 1.489 | 0.376 | 0.15 | 0.109 | 3–5 | 2 | 20 |
| Gly—Pro—Gly—Arg, (SEQ. I.D. NO.3) | 250 | 2.242 | 0.775 | 0.294 | 0.153 | 5 | 15 | >100 |
|  | 25 | 2.566 | 1.782 | 0.526 | 0.176 | 8–10 | 16 | '100 |
| Arg—Gly—Pro—Gly, SEQ. I.D. (NO.4) | 250 | 0.1 | 0.121 | 0.11 | 0.113 | 0 | 0 | 0 |
|  | 25 | 1.325 | 0.357 | 0.164 | 0.116 | 5 | 2 | 50 |
| Arg—Gly—Pro—Gly—Arg, (SEQ. I.D. NO.5) | 250 | 2.116 | 0.974 | 0.334 | 0.15 | 10 | 14 | >100 |
|  | 25 | 2.16 | 0.853 | 0.268 | 0.145 | 5–10 | 14 | >100 |
| PGR | 250 | 2.605 | 1.139 | 0.37 | 0.282 | 10–15 | 30 | >100 |
|  | 25 | 2.645 | 1.052 | 0.323 | 0.216 | 5–10 | 15 | >100 |
| AZT | 20 µM | 0.428 | 0.19 | 0.209 | 0.192 | 0–1 | 0 | 11 |
|  | 2 µM | 1.712 | 0.801 | 0.313 | 0.226 | 10–15 | 11 | >100 |
|  | 0.2 µM | 3 | 1.986 | 0.6 | 0.231 | 10 | 22 | >100 |
| Pos. control 1 |  | 2.466 | 1.732 | 0.689 | 0.27 | 10 | 15 | >100 |
| Pos. control 2 |  | 2.578 | 1.778 | 0.528 | 0.199 | 8–10 | 23 | >100 |
| Neg. control 1 |  | 0.193 |  |  |  |  | 0 |  |
| Neg. control 2 |  | 0.174 |  |  |  |  | 0 |  |

TABLE 4

HTLV IIIB/H9 Denmark

| PEPTIDE | CONC. µg/ml | p24 1/10 | p24 1/100 | p24 1/1,000 | p24 1/10,000 | % OF POS CELLS | # OF SYNCYTIA/WELL Day 9 |
|---|---|---|---|---|---|---|---|
| Tyr—Arg—Gly—Pro—Gly, (SEQ. I.D. NO.2) | 250 | 0.257 | 0.107 | 0.123 | 0.092 | 0 | 0 |
|  | 25 | 0.809 | 0.505 | 0.133 | 0.077 | 5 | 3 |
| Gly—Pro—Gly | 250 | 0.236 | 0.13 | 0.116 | 0.094 | 0 | 0 |
|  | 25 | 1.009 | 0.207 | 0.097 | 0.079 | 1–2 | 0 |
| Gly—Pro—Gly—Arg, (SEQ. I.D. NO.3) | 250 | 2.078 | 1.252 | 0.368 | 0.142 | 5–10 | 13 |
|  | 25 | 2.262 | 1.133 | 0.262 | 0.093 | 10 | 16 |
| Arg—Gly—Pro—Gly, (SEQ. I.D. NO.4) | 250 | 0.398 | 0.124 | 0.128 | 0.138 | 0 | 0 |
|  | 25 | 2.265 | 0.927 | 0.203 | 0.1 | 10 | 4 |
| Arg—Gly—Pro—Gly— (Arg, SEQ. I.D. NO.5) | 250 | 2.063 | 1.272 | 0.358 | 0.165 | 10 | 7 |
|  | 25 | 2.138 | 0.741 | 0.189 | 0.096 | 4–5 | 11 |
| Pro—Gly—Arg | 250 | 2.188 | 0.772 | 0.221 | 0.127 | 5 | 11 |
|  | 25 | 2.161 | 0.74 | 0.237 | 0.103 | 5 | 13 |
| AZT | 20 µM | 0.881 | 0.244 | 0.121 | 0.09 | 0.1–1 | 0 |
|  | 2 µM | 2.148 | 0.596 | 0.165 | 0.101 | 5–8 | 10 |
|  | 0.2 µM | 2.724 | 1.388 | 0.385 | 0.144 | 5–10 | 16 |
| Pos. control 1 |  | 2.71 | 1.202 | 0.276 | 0.14 | 4 | 11 |
| Pos. control 2 |  | 2.208 | 1.126 | 0.294 | 0.132 | 5 | 16 |
| Neg. control 1 |  | 0.106 |  |  |  |  | 0 |
| Neg. control 2 |  | 0.091 |  |  |  |  | 0 |

TABLE 5

ELI1/HUT

| PEPTIDE | CONC. µg/ml | p24 1/10 | p24 1/100 | p24 1/1,000 | p24 1/10,000 | PERCENTAGE OF POS CELLS |
|---|---|---|---|---|---|---|
| Try—Arg—Gly—Pro—Gly, (SEQ. I.D. NO.2) | 250 | 1.475 | 0.341 | 0.208 | 0.192 | 0.5–2 |
|  | 25 | 2.667 | 2.221 | 0.655 | 0.279 | 10 |
| Gly—Pro—Gly | 250 | 0.378 | 0.202 | 0.2 | 0.183 | 0.1 |
|  | 25 | 2.708 | 1.294 | 0.37 | 0.216 | 5–10 |
| Gly—Pro—Gly—Arg, (SEQ. I.D. NO.3) | 250 | 3 | 1.888 | 0.756 | 0.254 | 10–15 |
|  | 2 | 3 | 2.222 | 0.688 | 0.275 | 10 |

TABLE 5-continued

| | ELI1/HUT | | | | | |
|---|---|---|---|---|---|---|
| | CONC. | | p24 | | | PERCENTAGE |
| PEPTIDE | µg/ml | 1/10 | 1/100 | 1/1,000 | 1/10,000 | OF POS CELLS |
| Arg—Gly—Pro—Gly, (SEQ. I.D. NO.4) | 250 | 0.8 | 0.266 | 0.197 | 0.202 | 0.2–0.5 |
| | 25 | 3 | 1.701 | 0.595 | 0.248 | 10 |
| Arg—Gly—Pro—Gly—Arg, (SEQ. I.D. NO.5) | 250 | 3 | 1.999 | 0.788 | 0.339 | 10–15 |
| | 25 | 3 | 2.296 | 0.745 | 0.263 | 10–15 |
| Pro—Gly—Arg | 250 | 3 | 2.023 | 0.773 | 0.269 | 10–15 |
| | 25 | 3 | 2.192 | 0.671 | 0.242 | 15 |
| AZT | 20 µM | 1.023 | 0.312 | 0.221 | 0.243 | 10–15 |
| | 2 µM | 3 | 1.991 | 0.683 | 0.255 | 10 |
| | 0.2 µM | 3 | 2.016 | 0.795 | 0.373 | 10 |
| Pos. control 1 | | 3 | 2.238 | 0.934 | 0.353 | 10 |
| Pos. control 2 | | 3 | 2.238 | 0.934 | 0.353 | 10 |
| Neg. control 1 | | 0.201 | | | | |
| Neg. control 2 | | 0.235 | | | | |

TABLE 6

| | HTLV IIIB/H9 N.Y. | | | | |
|---|---|---|---|---|---|
| | CONC. | p24 | | PERCENTAGE OF | # OF SYNCYTIA/WELL |
| PEPTIDE | µg/ml | 1/10 | 1/100 | 1/1,000 | AG POS CELLS | Day 14 |
| Gly—Pro—Arg | 250 | >2.0 | 0.299 | 0.059 | 20–30 | 20 |
| | 25 | >2.0 | 0.616 | 0.154 | 30–40 | 85 |
| Gly—Pro—Gly, (SEQ. I.D. NO.6) | 250 | 0.523 | 0.052 | 0.007 | 30 | 20 |
| | 25 | 0.933 | 0.11 | 0.016 | 25–30 | 15 |
| Gly—Gly—Gly | 250 | >2.0 | 0.548 | 0.088 | 30–40 | 105 |
| | 25 | >2.0 | 1.89 | 0.415 | 40 | 90 |
| Pro, Gly | 250 | 0.691 | 0.068 | 0.01 | 40 | 0 |
| | 25 | 1.069 | 0.128 | 0.013 | 30–40 | 1 |
| Gly—Pro | 250 | >2.0 | 0.297 | 0.036 | 20 | 25 |
| | 25 | 1.673 | 0.187 | 0.016 | 20–25 | 12 |
| AZT | 20 µM | 0.003 | 0.007 | 0.005 | 0 | 0 |
| | 2 µM | 0.006 | 0 | 0.003 | 0.5–2 | 4 |
| | 0.2 µM | 1.562 | 0.218 | 0.039 | 30 | 29 |
| Pos. control | | 1.966 | 0.304 | 0.031 | 30–40 | 23 |
| Neg. control | | 0.006 | | | 0 | |

EXAMPLE 3

Interaction of Peptides Tyr-Arg-Gly-Pro-Gly, Gly-Pro-Gly and Arg-Gly-Pro-Gly With Herpes Simplex Virus (HSV) Replication To determine the specificity and toxicity of the peptides, Tyr-Arg-Gly-Pro-Gly (Seq. I.D. No. 2), Gly-Pro-Gly and Arg-Gly-Pro-Gly (Seq. I.D. No. 4) were tested in (1) a plaque reduction assay and (2) a yield inhibition assay of herpes simplex virus type I (HSV-1) strain McIntyre.

Plaque reduction of HSV-1 was performed on monolayers of green monkey kidney (GMK) AH1 cells grown in 5 cm petri dishes. A stock of HSV-1 was diluted to 100–200 plaque forming units (pfu) per ml and allowed to adsorb to the cells in the presence of the respective peptide at concentrations of 250 and 25 µg/ml or without any peptide (control) for 1 hour at 20° C. Thereafter, the inoculum was replaced by growth medium (Eagle's Minimum Essential Medium (MEM) supplemented with 2% newborn calf serum, antibiotics and 1% methylcellulose) with the respective peptide. The number of plaques was counted after 4 days of incubation at 37° C.

The yield inhibition assay was performed as follows: HSV-1 was inoculated at a multiplicity of 0.5 pfu per GMK cell in the presence of the respective peptide at concentrations of 250 and 25 µg/ml. Virus adsorption was performed for 60 min. at room temperature. The cells were then rinsed five times with Hanks' Balanced Salt Solution (BSS) and incubated in a 5% $CO_2$ atmosphere at 37° C. with maintenance medium containing either peptides or acyclovir, according to the methods described in "Proceedings of a Symposium on Acyclovir", The American Journal of Medicine, Jul. 20, (1982) which is incorporated herein by reference, or without any additives. Twenty-four hours p.i. the cells were freeze-thawed, scraped into the medium and tested for virus yield by the infectivity assay as outlined in Example 2. The results are shown in Table 7 where the plaque reduction values are the mean of two cultures and the yield of HSV-1 after 24 hours is the mean of two determinations and the values are presented in millions of pfu/ml.

With regard to plaque reduction and virus yields, as shown in Table 7, it is clearly evident that peptides Tyr-Arg-Gly-Pro-Gly, Gly-Pro-Gly and Arg-Gly-Pro-Gly did not reduce the capacity of HSV-1 to replicate in GMK cells; the peptides are thus specific for HIV-1. However, yields of HSV-1 were significantly reduced by acyclovir, 2 µM, which is a specific antiherpes drug. Additionally, the peptides did not display toxicity towards the GMK cells as indicated by morphological examination by phase contrast microscopy and by an unchanged yield of HSV-1 with or without peptides in the medium.

It is evident from the foregoing experiments that the peptides of the present invention are effective in specifically preventing HIV infection of cells susceptible to HIV infection.

TABLE 7

EFFECT OF PEPTIDES ON HERPES SIMPLEX VIRUS INFECTION

| PEPTIDE | μg/ml | PLAQUE REDUCTION NO. OF PLAQUES | PERCENT OF CONTROL | YIELD OF HSV AFTER 24 HOURS | PERCENT OF CONTROL |
|---|---|---|---|---|---|
| YRGPG | 250 | 147 | 90 | 33 | 106 |
|  | 25 | 152 | 93 | 26 | 84 |
| GPG | 250 | 161 | 99 | 29 | 94 |
|  | 25 | 158 | 97 | 30 | 97 |
| RGPG | 250 | 143 | 88 | 25 | 81 |
|  | 25 | 136 | 83 | 32 | 103 |
| Acyclovir 2 μM |  | Not Done |  | 0.9 | 3 |
| Control |  | 163 |  | 31 |  |

EXAMPLE 4

Comparison of the Peptides in Their Carboxy and Amido Forms

In order to determine if peptides containing a carboxy-terminal carboxy group rather than an amido group were functional, a side by side comparison of the two forms of Gly-Pro-Gly and Pro-Gly was performed.

The peptides in their carboxy and amido forms were obtained from Bachem Feinchemikalien AG (Switzerland, GPG-NH$_2$ Bachem, GPG-COOH, Bachem, PG-NH$_2$ Bachem and PG-COOH Bachem) and Syntello (Sweden, GPG-NH$_2$ Syntello). The effectiveness of the peptides was determined by both p24 production and syncytia formation as described in Example 2. The results obtained are presented in Tables 8 and 9. Table 8 shows the results obtained comparing both forms of Gly-Pro-Gly utilizing HTLV IIIB/H9 N.Y. Table 9 shows the results obtained comparing both forms of Pro-Gly utilizing HTLV IIIB/H9 N.Y.

In tables 8 and 9, the p24 content of the supernatants of infected cells was determined by diluting the supernatants in serial tenfold dilutions (1/10, 1/100, 1/1,000) and analyzing by ELISA as described in Example 2. Results are indicated by the absorbance values (454 nm) of respective dilutions.

From the data presented in Tables 8 and 9 it is clear that only the amido forms of the peptides have anti-HIV activity. The carboxy forms of the peptides have no antiviral activity whatsoever.

Further, it was seen by phase contrast microscopy, that the carboxy form of the peptides, in the concentrations indicated in Tables 8 and 9, had no toxic effects on the cells. Consequently, the results obtained with the amido forms, were not due to a nonspecific toxic effect of the peptides.

TABLE 8

EFFECT OF AMIDO AND CARBOXY FORMS OF GPG ON HTLV IIIB/H9 N.Y.

| PEPTIDE | CONC. mM | p24 1/10 | p24 1/100 | p24 1/1000 | # OF SYNCYTIA/ WELL Day 7 |
|---|---|---|---|---|---|
| GPG—NH$_2$ Bachem | 4 | 0.087 | 0.079 | 0.082 | 0 |
|  | 1 | 0.070 | 0.081 | 0.08 | 0 |
|  | 0.25 | 0.063 | 0.07 | 0.074 | 0 |
|  | 0.0625 | 0.404 | 0.131 | 0.11 | 0 |
|  | 0.015 | >2.0 | 1.259 | 0.342 | 61 |
| GPG—COOH Bachem | 4 | 1.552 | 1.007 | 0.348 | 64 |
|  | 1 | 1.610 | 1.135 | 0.299 | 67 |
|  | 0.25 | 1.404 | 0.648 | 0.159 | 36 |
|  | 0.0625 | >2.0 | 0.797 | 0.221 | 86 |
|  | 0.015 | 1.485 | 0.397 | 0.104 | ND |
| GPG—NH$_2$ Syntello | 4 | 0.075 | 0.076 | 0.083 | 0 |
|  | 1 | 0.081 | 0.081 | 0.085 | 0 |
|  | 0.25 | 0.094 | 0.075 | 0.08 | 1 |
|  | 0.0625 | 1.271 | 0.247 | 0.112 | 1 |
|  | 0.015 | >2.0 | 1.145 | 0.274 | 68 |
| Pos Control |  | 1.561 | 0.708 | 0.164 | 35 |
| " |  | >2.0 | 0.883 | 0.19 | 42 |
| " |  | >2.0 | 1.186 | 0.254 | 31 |
| " |  | >2.0 | 1.155 | 0.296 | 44 |
| Neg control |  | 0.082 |  |  | 0 |
| " |  |  |  |  | 0 |
| AZT | 0.02 | 0.166 | 0.087 | 0.083 | 5 |
| AZT | 0.002 | 1.333 | 0.427 | 0.135 | 11 |
| AZT | 0.0002 | >2.0 | 1.181 | 0.246 | 26 |

TABLE 9

EFFECT OF AMIDO AND CARBOXY FORMS OF PG ON HTLV IIIB-H9 N.Y.

| PEPTIDE | CONC. mM | p24 1/10 | p24 1/100 | p24 1/1000 | # OF SYNCYTIA/WELL Day 7 |
|---|---|---|---|---|---|
| PG—NH₂ | 4 | 0.077 | 0.069 | 0.08 | 1 |
| Bachem | 1 | 0.081 | 0.066 | 0.063 | 0 |
|  | 0.25 | 1.639 | 0.584 | 0.132 | 68 |
|  | 0.0625 | >2.0 | 0.758 | 0.168 | 78 |
|  | 0.015 | >2.0 | 0.575 | 0.135 | 89 |
| PG—COOH | 4 | >2.0 | 0.973 | 0.249 | 83 |
| Bachem | 1 | 1.397 | 0.484 | 0.132 | 72 |
|  | 0.25 | 1.229 | 0.301 | 0.125 | ND |
|  | 0.0625 | 1.413 | 0.662 | 0.155 | ND |
|  | 0.015 | 1.483 | 0.554 | 0.133 | ND |
| Pos Control |  | 1.355 | 0.361 | 0.1 | 95 |
| " |  | 1.629 | 0.639 | 0.161 | 74 |
| " |  | 1.596 | 0.751 | 0.162 | 90 |
| " |  | >2.0 | 1.254 | 0.294 | ND |
| Neg control |  | 0.076 |  |  |  |
| " |  | 0.069 |  |  |  |
| AZT | 0.02 | 0.166 | 0.087 | 0.083 | 5 |
| AZT | 0.002 | 1.333 | 0.427 | 0.135 | 11 |
| AZT | 0.0002 | >2.0 | 1.181 | 0.246 | 26 |

EXAMPLE 5

Effect of Combining AZT and the Peptides

In order to determine the effect of combinations of the peptides with known anti-HIV drugs, HTLV-IIIB in H9 cells, SF-2 in HUT cells and different street strains of HIV-1 in human peripheral blood lymphocyte cell cultures (HPBLC) were treated with Gly-Pro-Gly or Pro-Gly alone and in combination with AZT.

The inhibitory effects of Gly-Pro-Gly and AZT, Table 11 alone and in combination, on HTLV-IIIB replication in H9 cells are shown in Tables 10 and 11. The results in Tables 10 and 11 were obtained as described in Example 2. The supernatants were tested for p24 on day 8 p.i. Supernatants were serially diluted (1/5, 1/50 and 1/500) and analyzed by ELISA as described in Example 2. Results are indicated by the absorbance values (454 nm) of the respective dilutions.

Figure 1B:
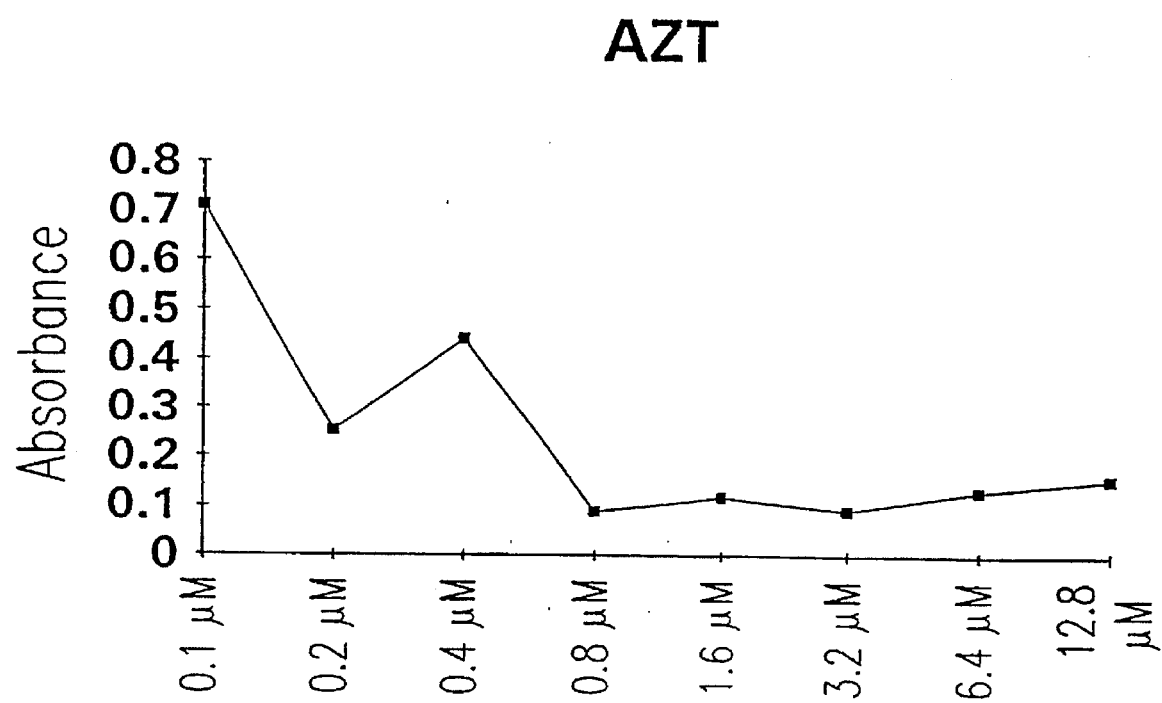
Figure 1C:
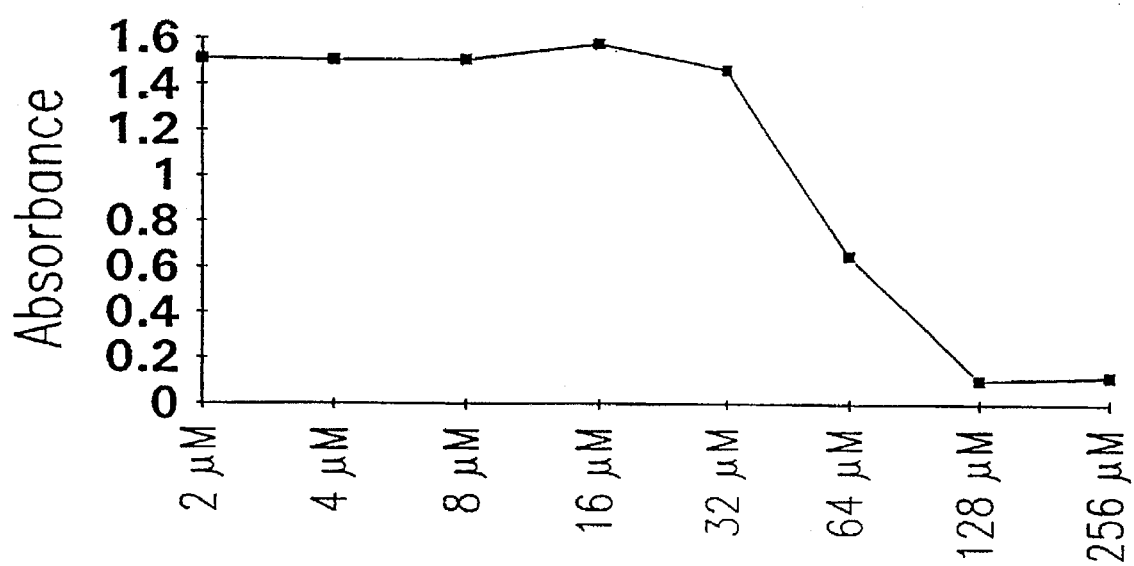
Figure 1D:
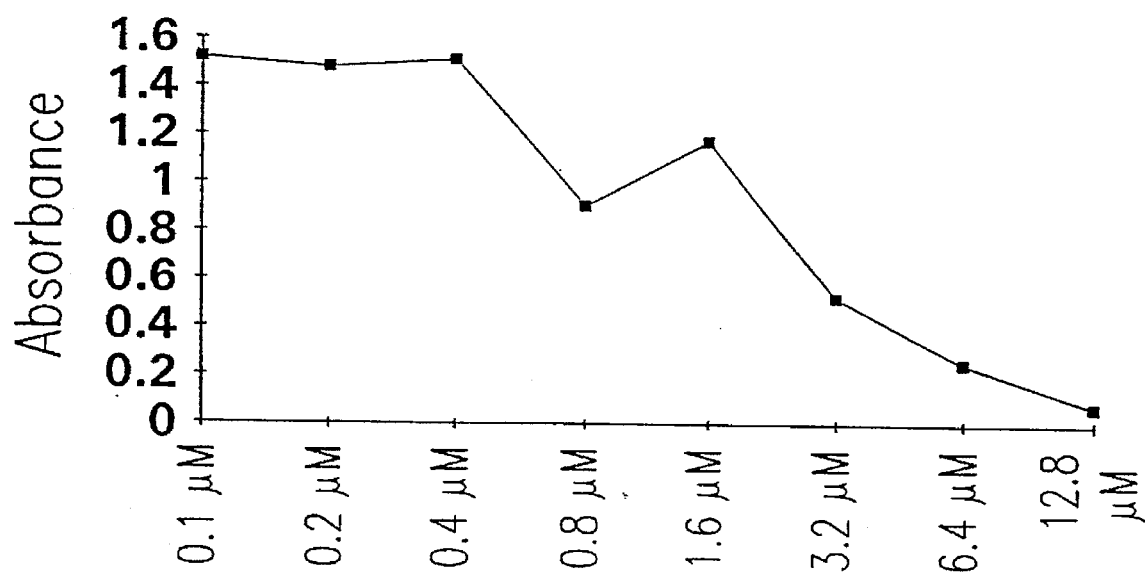

The inhibitory effects of Gly-Pro-Gly and AZT, on HTLV-IIIB replication in H9 cells was further investigated in dose response experiments. Thereby, approximate $ID_{50}$ values (the inhibitory dose of drug reducing virus yield to 50%) was calculated on the basis of the concentration of p24 antigen as determined by absorbance at 454 nm in supernatants of infected cells diluted 1/5 from cultures of cells 8 and 12 days post-infection. On day 8, p24 antigen was reduced by 50% at a concentration of 4 μM Gly-Pro-Gly and 0.4 μM AZT (FIGS. 1a and 1b). Twelve days after infection corresponding values for Gly-Pro-Gly were 64 μM and 3.2 μM for AZT respectively (FIGS. 1c and 1d)

Figure 2:
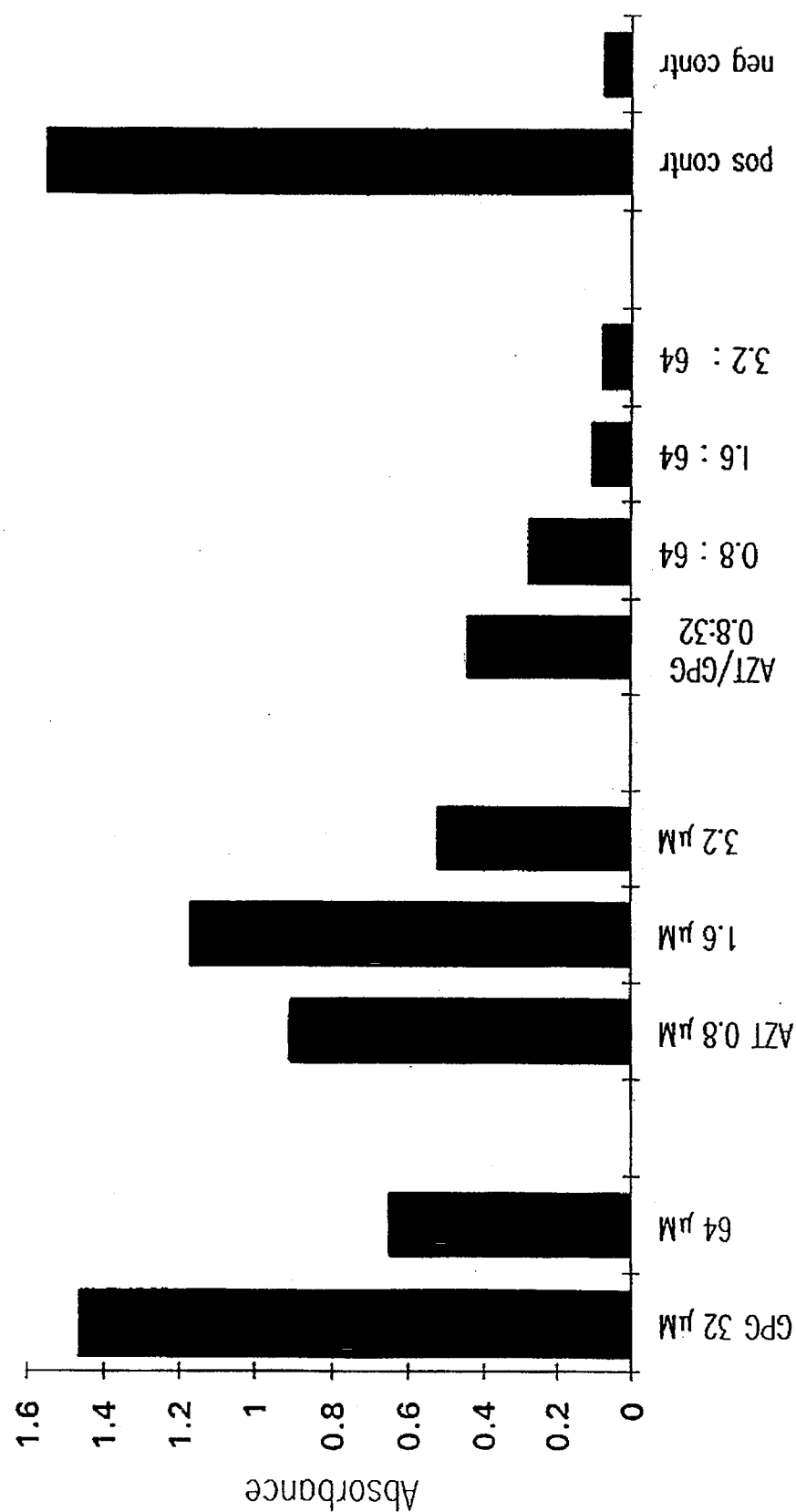
FIG. 2 is a bar graph depicting the synergistic effect of Gly-Pro-Gly and AZT.

By combining Gly-Pro-Gly and AZT in ratios of 20:1, 2:1, and fixed AZT concentrations (0.8 and 1.6 μM) with variable Gly-Pro-Gly concentrations (2–256 μM) as shown in Tables 10 and 11, both additive and synergistic inhibitory effects on HIV replication were evident. Thus, p24 levels (assayed on day 12 post-infection) in cultures with 32–64 μM Gly-Pro-Gly mixed with media containing equal to or less than 3.2 μM AZT were significantly lower than the controls of p24 in cultures with either of the drugs alone (FIG. 2).

TABLE 10

EFFECT OF GLY—PRO—GLY and AZT on HTLV IIIB-H9 N.Y

| PEPTIDE | CONC. μM | p24 1/5 | p24 1/50 | p24 1/500 |
|---|---|---|---|---|
| GPG | 2 | 1.385 | 0.429 | 0.207 |
|  | 4 | 0.786 | 0.202 | 0.139 |
|  | 8 | 0.287 | 0.100 | 0.077 |
|  | 16 | 0.337 | 0.132 | 0.117 |
|  | 32 | 0.176 | 0.143 | 0.089 |
|  | 64 | 0.129 | 0.150 | 0.136 |
|  | 128 | 0.175 | 0.098 | 0.111 |
|  | 256 | 0.180 | 0.075 | 0.123 |
| AZT/GPG | 0.1:2 | 0.251 | 0.191 | 0.140 |
|  | 0.2:4 | 0.212 | 0.128 | 0.102 |
|  | 0.4:8 | 0.133 | 0.071 | 0.072 |
|  | 0.8:16 | 0.139 | 0.117 | 0.082 |
|  | 1.6:32 | 0.117 | 0.094 | 0.103 |
|  | 3.2:64 | 0.202 | 0.135 | 0.133 |
|  | 6.4:128 | 0.111 | 0.095 | 0.209 |
|  | 12.8:256 | 0.092 | 0.100 | 0.076 |
| AZT/GPG | 0.1:0.2 | 0.229 | 0.078 | 0.086 |
| AZT/GLY—PRO—GLY | 0.2:0.4 | 0.181 | 0.086 | 0.067 |
|  | 0.4:0.8 | 0.210 | 0.081 | 0.066 |
|  | 0.8:1.6 | 0.100 | 0.076 | 0.069 |
|  | 1.6:3.2 | 0.106 | 0.081 | 0.087 |
|  | 3.2:6.4 | 0.178 | 0.092 | 0.088 |
|  | 6.4:12.8 | 0.110 | 0.090 | 0.086 |
|  | 12.8:25.6 | 0.086 | 0.100 | 0.090 |
| AZT | 0.1 | 0.710 | 0.175 | 0.090 |
|  | 0.2 | 0.253 | 0.094 | 0.080 |
|  | 0.4 | 0.441 | 0.114 | 0.099 |
|  | 0.8 | 0.089 | 0.087 | 0.086 |
|  | 1.6 | 0.120 | 0.087 | 0.093 |
|  | 3.2 | 0.091 | 0.099 | 0.085 |
|  | 6.4 | 0.132 | 0.081 | 0.094 |
|  | 12.8 | 0.156 | 0.113 | 0.072 |
| AZT/GPG | 1.6:2 | 0.162 | 0.141 | 0.067 |
|  | 1.6:4 | 0.134 | 0.105 | 0.064 |
| AZT/GPG | 1.6:8 | 0.151 | 0.077 | 0.066 |
|  | 1.6:16 | 0.132 | 0.133 | 0.078 |
|  | 1.6:32 | 0.143 | 0.100 | 0.090 |
|  | 1.6:64 | 0.129 | 0.111 | 0.103 |
|  | 1.6:128 | 0.116 | 0.077 | 0.077 |
|  | 1.6:256 | 0.087 | 0.069 | 0.119 |
|  | 0.8:2 | 0.089 | 0.066 | 0.098 |
|  | 0.8:4 | 0.103 | 0.063 | 0.117 |
|  | 0.8:8 | 0.086 | 0.063 | 0.065 |
|  | 0.8:16 | 0.094 | 0.083 | 0.096 |
|  | 0.8:32 | 0.109 | 0.082 | 0.083 |
|  | 0.8:64 | 0.268 | 0.155 | 0.106 |
|  | 0.8:128 | 0.095 | 0.078 | 0.089 |
|  | 0.8:256 | 0.084 | 0.072 | 0.070 |
| Pos contr |  | 1.274 | 0.409 | 0.122 |
|  |  | 0.926 | 0.211 | 0.085 |
|  |  | 1.179 | 0.315 | 0.108 |
|  |  | 0.793 | 0.184 | 0.193 |
| neg contr |  | 0.085 |  |  |
|  |  | 0.092 |  |  |

TABLE 11

EFFECT OF GPLY—PRO—GLY AND AZT ON HTLV IIIB/H9 N.Y.

| PEP-TIDE | CONC. μM | p24 1/5 | p24 1/50 | p24 1/500 | # OF SYNCYTIA/WELL Day 7 | Day 10 |
|---|---|---|---|---|---|---|
| GPG | 2 | 1.512 | 1.360 | 0.632 | 61 | >400 |
|  | 4 | 1.506 | 1.193 | 0.435 | 35 | >400 |
|  | 8 | 1.507 | 1.099 | 0.306 | 23 | >400 |
|  | 16 | 1.575 | 1.207 | 0.439 | 14 | >400 |

TABLE 11-continued

EFFECT OF GPLY—PRO—GLY AND AZT ON HTLV IIIB/H9 N.Y.

| PEP-TIDE | CONC. µM | p24 1/5 | p24 1/50 | p24 1/500 | # OF SYNCYTIA/WELL Day 7 | # OF SYNCYTIA/WELL Day 10 |
|---|---|---|---|---|---|---|
| | 32 | 1.462 | 1.060 | 0.310 | 1 | 151 |
| | 64 | 0.650 | 0.133 | 0.060 | 0 | 9 |
| | 128 | 0.104 | 0.059 | 0.066 | 0 | 0 |
| | 256 | 0.120 | 0.081 | 0.078 | 0 | 0 |
| AZT/ | 0.1:2 | 1.451 | 0.968 | 0.216 | 5 | 135 |
| GPG | 0.2:4 | 1.378 | 0.768 | 0.178 | 0 | 87 |
| | 0.4:8 | 1.263 | 0.469 | 0.159 | 0 | 35 |
| | 0.8:16 | 1.507 | 1.046 | 0.293 | 12 | >200 |
| | 1.6:32 | 0.194 | 0.071 | 0.059 | 0 | 0 |
| | 3.2:64 | 0.077 | 0.056 | 0.060 | 0 | 0 |
| | 6.4:128 | 0.079 | 0.060 | 0.055 | 0 | 0 |
| | 12.8:256 | 0.123 | 0.084 | 0.080 | 0 | 0 |
| AZT/ | 0.1:0.2 | 1.445 | 0.826 | 0.235 | 15 | >200 |
| GPG | 0.2:0.4 | 1.491 | 1.018 | 0.280 | 15 | >200 |
| | 0.4:0.8 | 1.469 | 0.971 | 0.274 | 17 | >200 |
| | 0.8:1.6 | 1.273 | 0.456 | 0.158 | 1 | >200 |
| | 1.6:3.2 | 1.015 | 0.240 | 0.099 | 0 | 15 |
| | 3.2:6.4 | 1.410 | 0.807 | 0.199 | 0 | 28 |
| | 6.4:12.8 | 0.303 | 0.098 | 0.074 | 0 | 31 |
| | 12.8:25.6 | 0.119 | 0.074 | 0.102 | 0 | 0 |
| AZT | 0.1 | 1.520 | 1.174 | 0.347 | 40 | >200 |
| | 0.2 | 1.480 | 0.968 | 0.258 | 34 | >200 |
| | 0.4 | 1.512 | 1.066 | 0.294 | 24 | >200 |
| | 0.8 | 0.905 | 0.241 | 0.092 | 3 | 71 |
| | 1.6 | 1.17 | 0.340 | 0.105 | 0 | 88 |
| | 3.2 | 0.522 | 0.136 | 0.074 | 0 | 37 |
| | 6.4 | 0.247 | 0.083 | 0.067 | 0 | 14 |
| | 12.8 | 0.075 | 0.058 | 0.061 | 0 | 0 |
| AZT/ | 1.6:2 | 0.849 | 0.191 | 0.079 | 0 | 39 |
| GPG | 1.6:4 | 1.368 | 0.591 | 0.161 | 0 | 175 |
| | 1.6:8 | 1.205 | 0.295 | 0.090 | 0 | 38 |
| | 1.6:16 | 0.504 | 0.114 | 0.065 | 0 | 38 |
| | 1.6:32 | 1.058 | 0.279 | 0.256 | 0 | 34 |
| | 1.6:64 | 0.106 | 0.103 | 0.084 | 0 | 0 |
| | 1.6:128 | 0.074 | 0.067 | 0.061 | 0 | 0 |
| | 1.6:256 | 0.074 | 0.053 | 0.055 | 0 | 0 |
| AZT/ | 0.8:2 | 0.807 | 0.170 | 0.103 | 1 | 66 |
| GPG | 0.8:4 | 1.594 | 0.770 | 0.154 | 0 | 93 |
| | 0.8:8 | 1.395 | 0.568 | 0.159 | 0 | 53 |
| | 0.8:16 | 1.388 | 0.446 | 0.107 | 0 | 58 |
| | 0.8:32 | 0.442 | 0.161 | 0.066 | 0 | 5 |
| | 0.8:64 | 0.273 | 0.107 | 0.082 | 0 | 14 |
| | 0.8:128 | 0.135 | 0.075 | 0.063 | 0 | 0 |
| pos contr | | 1.552 | 1.446 | 0.790 | 82 | 155 |
| | | 1.546 | 1.460 | 0.635 | 8 | 47 |
| | | 1.584 | 1.299 | 0.644 | 32 | |
| | | 1.578 | 1.485 | 0.704 | 38 | |
| neg contr | | 0.073 | | | | |
| | | 0.091 | | | | |

EXAMPLE 6

Treatment of Street Strains of HIV with the Peptides

The results of the neutralization experiments of the five street strains of HIV-1 by Gly-Pro-Gly are shown in Table 12. Five isolates of HIV-1 (street strains) were recovered by cocultivation of $10^7$ peripheral blood mononuclear cells (PBMC) from five different HIV-1 infected Swedish individuals with $10^7$ blood donor PBMC, which had been stimulated for three days with 2.5 µg/ml of phytohemagglutinin (PHA; DIFCO Detroit, Mich.). Cell cultures were maintained in RPMI 1640 medium supplemented with 10% fetal calf serum (FCS), interleukin-2 (10% T cell growth factor, Cellular Products, Buffalo, N.Y.), 2 µg/ml of Polybrene, antibiotics and 5 µg/ml of hydrocortisone acetate. One half of the medium was replaced every third to fourth day and fresh PHA-stimulated cells were added at intervals of 7 days. No indication of syncytia on PBMC was seen with either of the isolates. The culture supernatants were continuously assayed for HIV-1 p24 antigen according to the manufacturer's instructions (Abbot) and when positive, the virus isolates were frozen as stocks at $-90°$ C. End point titers of the patient isolates ranged from 100 to 400 $TCIDS_{50}$. Stock virus of these isolates were diluted to 100 $TCID_{50}$ and mixed with serial fourfold dilutions of Gly-Pro-Gly starting at 4 mM and serial tenfold dilutions of AZT starting at 20 µM. Then the virus-drug mixtures were added to $10^6$ stimulated blood donor PBMC according to the method described in Example 2. Thus, after adsorption of virus at $4°$ C. and $37°$ C. respectively, PBMC were washed once and placed in 24 well multidish plates with 2 ml of PBMC medium containing the drugs (Gly-Pro-Gly and AZT) at the dilutions indicated in Table 12. Thirteen days after infection, supernatants of infected cells were collected and assayed by ELISA as described in Example 2 in fourfold dilutions for the presence of HIV-1 p24 antigen.

The results presented in Table 12 indicate that the peptides are effective at treating street strains of HIV. The peptides are further useful at treating unrelated HIV strains and thus have wide applicability as therapeutic agents against HIV.

TABLE 12

EFFECT OF GPG ON STREET STRAINS OF HIV-1

| VIRUS STRAIN | ANTIVIRUS SUBSTANCE | CONC. µM | p24 1/5 | p24 1/50 | p24 1/500 |
|---|---|---|---|---|---|
| 73 | none | | 0.962 | 0.29 | 0.083 |
| 73 | none | | 1.031 | 0.289 | 0.085 |
| 73 | AZT | 20 | 0.106 | 0.113 | 0.063 |
| 73 | AZT | 2 | 0.152 | 0.085 | 0.051 |
| 73 | AZT | 0.2 | 0.41 | 0.102 | 0.058 |
| 73 | GPG | 4000 | 0.096 | 0.062 | 0.052 |
| 73 | GPG | 1000 | 0.134 | 0.066 | 0.056 |
| 73 | GPG | 250 | 0.741 | 0.136 | 0.059 |
| 73 | GPG | 62.5 | 0.906 | 0.2 | 0.072 |
| 73 | GPG | 15 | 1.157 | 0.464 | 0.111 |
| NEG CONTROL | | | 0.059 | | |
| 5220 | none | | 1.49 | 0.756 | 0.129 |
| 5220 | none | | 1.481 | 0.931 | 0.175 |
| 5220 | AZT | 20 | 0.226 | 0.135 | 0.073 |
| 5220 | AZT | 2 | 1.179 | 0.278 | 0.075 |
| 5220 | AZT | 0.2 | 1.492 | 0.664 | 0.101 |
| 5220 | GPG | 4000 | 0.292 | 0.085 | 0.069 |
| 5220 | GPG | 1000 | 0.267 | 0.065 | 0.059 |
| 5220 | Gly—Pro—Gly | 250 | 1.436 | 0.648 | 0.118 |
| 5220 | Gly—Pro—Gly | 62.5 | 1.4 | 0.415 | 0.098 |
| 5220 | Gly—Pro—Gly | 15 | 1.435 | 0.674 | 0.125 |
| NEG CONTROL | | | 0.05 | | |
| 5004 | none | | 1.295 | 0.375 | 0.084 |
| 5004 | none | | 1.282 | 0.491 | 0.112 |
| 5004 | AZT | 20 | 0.083 | 0.053 | 0.064 |
| 5004 | AZT | 2 | 0.513 | 0.087 | 0.071 |
| 5004 | AZT | 0.2 | 1.218 | 0.333 | 0.078 |
| 5004 | Gly—Pro—Gly | 4000 | 0.115 | 0.157 | 0.068 |
| 5004 | Gly—Pro—Gly | 1000 | 0.432 | 0.079 | 0.065 |
| 5004 | Gly—Pro—Gly | 250 | 1.037 | 0.198 | 0.07 |
| 5004 | Gly—Pro—Gly | 62.5 | 1.286 | 0.49 | 0.113 |
| 5004 | Gly—Pro—Gly | 15 | 1.333 | 0.498 | 0.113 |
| NEG CONTROL | | | 0.077 | | |
| 5049 | none | | 1.368 | 0.939 | 0.164 |
| 5049 | none | | 1.336 | 0.509 | 0.116 |
| 5049 | AZT | 20 | 0.183 | 0.06 | 0.047 |
| 5049 | AZT | 2 | 1.3 | 0.335 | 0.08 |
| 5049 | AZT | 0.2 | 1.402 | 0.55 | 0.105 |

TABLE 12-continued

EFFECT OF GPG ON STREET STRAINS OF HIV-1

| VIRUS STRAIN | ANTIVIRUS SUBSTANCE | CONC. µM | p24 1/5 | 1/50 | 1/500 |
|---|---|---|---|---|---|
| 5049 | Gly—Pro—Gly | 4000 | 0.192 | 0.06 | 0.057 |
| 5049 | GPG | 1000 | 0.451 | 0.096 | 0.049 |
| 5049 | GPG | 250 | 1.335 | 0.308 | 0.069 |
| 5049 | GPG | 62.5 | 1.538 | 0.482 | 0.087 |
| 5049 | GPG | 15 | >3.0 | 0.984 | 0.164 |
| NEG CONTROL | | | 0.061 | | |
| 5092 | none | | 1.489 | 0.427 | 0.116 |
| 5092 | none | | 1.575 | 0.503 | 0.094 |
| 5092 | AZT | 20 | 0.09 | 0.065 | 0.07 |
| 5092 | AZT | 2 | 0.606 | 0.113 | 0.113 |
| 5092 | AZT | 0.2 | 1.439 | 0.36 | 0.09 |
| 5092 | GPG | 4000 | 0.117 | 0.052 | 0.053 |
| 5092 | GPG | 1000 | 0.141 | 0.066 | 0.055 |
| 5092 | GPG | 250 | 1.228 | 0.211 | 0.079 |
| 5092 | GPG | 62.5 | 1.397 | 0.384 | 0.091 |
| 5092 | GPG | 15 | 1.502 | 0.693 | 0.124 |
| NEG CONTROL | | | 0.062 | | |
| | BACKGROUND ABSORBANCE = 0.068 | | | | |

EXAMPLE 7

Treatment of Simian Immunodeficiency Virus by the Peptides

In addition to the antiviral effect of Gly-Pro-Gly and Pro-Gly shown for HTLV-IIIB in H9 cells, SF-2 in HUT cells and different street strains of HIV-1 in HPBLC, as shown in Example 6, Gly-Pro-Gly and Pro-Gly also inhibited the replication of simian immunodeficiency virus (SIV) as shown in two separate experiments. The results are depicted in Tables 13 and 14.

In these experiments $1 \times 10^6$ HPBLC were infected with suspensions of undiluted SIV (provided by Dr. Eva Maria Fenyo, Karolinska Institute, University of Stockholm) according to procedures outlined in Example 2. Two weeks post-infection, supernatants of infected cells were collected and assayed for p24 antigen by the Abbot HIV-1 antigen assay according to the manufacturer's instructions. The p24 content of the supernatants was measured by ELISA of serially diluted supernatant samples (1/5, 1/50, 1/500) as indicated by absorbance values (454 nm) of respective dilutions.

The results presented in Tables 13 and 14 show that in these experiments, SIV was inhibited by 1 mM Gly-Pro-Gly and by 4 mM Pro-Gly i.e. to a lesser extent than HTLV-IIIB in H9 cells, by the same peptides. These results indicate that the peptides are useful in studying animal models of HIV and AIDS.

TABLE 13

EFFECT OF GLY—PRO—GLY AND PRO—GLY ON SIV

| VIRUS/CELL | PEPTIDE | CONC. mm | p24 1/1 | 1/10 |
|---|---|---|---|---|
| SIV/HPBLC | GPG | 4 | 0.064 | 0.053 |
| | | 1 | 0.149 | 0.064 |
| | | 0.25 | 1.142 | 0.312 |
| | | 0.0625 | 1.361 | 0.776 |
| | | 0.015 | 1.392 | 0.936 |
| | PG | 4 | 0.664 | 0.156 |
| | | 1 | 1.316 | 0.821 |
| | | 0.25 | 1.427 | 0.966 |
| | | 0.0625 | 1.416 | 0.795 |
| | | 0.015 | 1.581 | 0.804 |
| pos contr | | 0 | 1.272 | 0.578 |
| SIV/HPBLC | | 0 | 1.339 | 0.736 |
| | | 0 | 1.336 | 0.949 |
| | | 0 | 1.391 | 0.737 |
| HTLV-111/H9 | GPG | 4 | 0.052 | 0.048 |
| | | 1 | 0.062 | 0.047 |
| | | 0.25 | 0.051 | 0.05 |
| | | 0.0625 | 0.053 | 0.044 |
| | | 0.015 | 0.058 | 0.048 |
| HTLV-111/H9 | PG | 4 | 0.089 | 0.056 |
| | | 1 | n.d. | n.d. |
| | | 0.25 | 0.056 | 0.048 |
| | | 0.0625 | 0.059 | 0.054 |
| | | 0.015 | 0.078 | 0.122 |

TABLE 14

EFFECT OF GPG AND PG ON SIV

| VIRUS | PEPTIDE | CONC. µM | p24 1/1 | 1/10 |
|---|---|---|---|---|
| SIV | GPG | 4 | 0.035 | 0.035 |
| | | 1 | 0.043 | 0.032 |
| | | 0.25 | 0.509 | 0.090 |
| | | 0.0625 | 1.133 | 0.792 |
| | | 0.015 | 1.173 | 0.998 |
| | PG | 4 | 0.093 | 0.042 |
| | | 1 | 1.099 | 0.985 |
| | | 0.25 | 1.210 | 0.903 |
| | | 0.0625 | 1.127 | 0.908 |
| | | 0.015 | 1.159 | 0.755 |
| pos contr | | 0 | 1.225 | 0.988 |
| | | 0 | 1.151 | 1.018 |
| | | 0 | 1.573 | 0.937 |
| | | 0 | 1.122 | 0.749 |
| neg.cont | | | 0.034 | n.d. |
| SIV | AZT | 20 | 0.036 | 0.058 |
| | | 2 | 0.976 | 0.274 |
| | GPG | 4 | 0.035 | 0.035 |
| | | 0.2 | 1.102 | 0.826 |

EXAMPLE 8

Peptide toxicity

Figure 3:
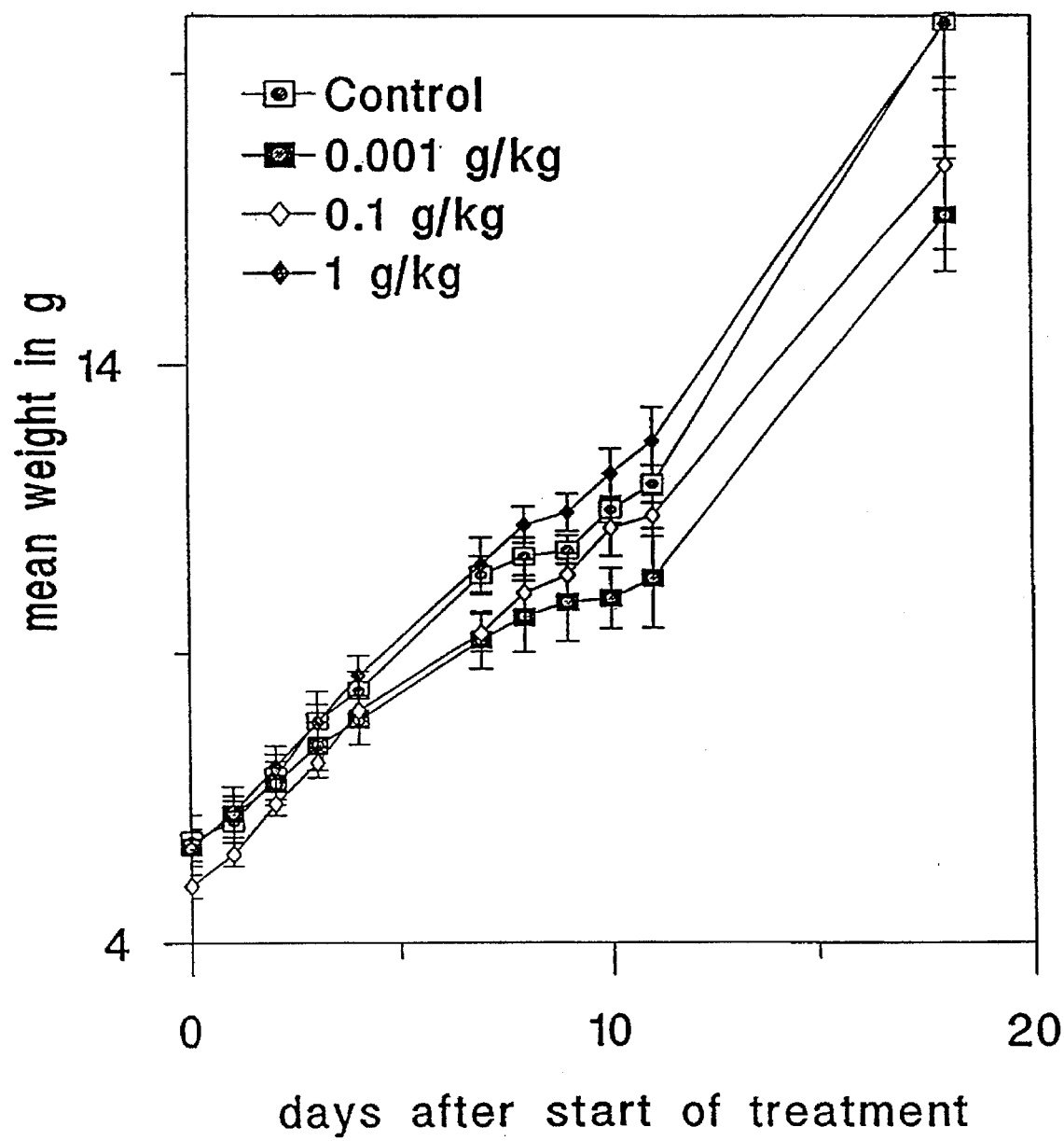
FIG. 3 is a graph depicting the growth of mice treated with Gly-Pro-Gly.

In an in vivo test of the toxicity of Gly-Pro-Gly, groups of mice were given intraperitoneal injections of the substance starting at an age of 6 days. The amount of Gly-Pro-Gly given and the increase in weight is given in Table 15. FIG. 3 also graphically depicts the results. These data show that, compared with controls, there is no significant influence of Gly-Pro-Gly on the growth of mice. The peptides are thus nontoxic even when given in large doses.

TABLE 15

INCREASE IN WEIGHT OF MICE TREATED WITH GPG

| | Group 1 | Group 2 | Group 3 | Group 4 |
|---|---|---|---|---|
| | | Amount of GPG given, in g | | |
| Date | Control | 0.001 | 0.1 | 1 |
| Feb. 25 | 5.14 | 6.2 | 4.71 | 5.6 |
| | 5.47 | 5.27 | 4.95 | 5.94 |
| | 5.72 | 5.52 | 4.94 | 5.35 |
| | 6.04 | 5.86 | 5.19 | 5.6 |
| | 6.37 | 5.56 | 4.85 | 5.73 |
| | 5.93 | 5.57 | 5.25 | 5.52 |
| Mean | 5.78 | 5.66 | 4.98 | 5.62 |
| SD | 0.44 | 0.32 | 0.20 | 0.20 |
| Date | | | | |
| Feb. 26 | 6.62 | 6.02 | 5.54 | 6.78 |
| | 6.46 | 6.8 | 5.48 | 5.5 |
| | 6.06 | 6.11 | 5.27 | 6.1 |
| | 6.00 | 6.01 | 5.85 | 6.3 |
| | 5.66 | 6.4 | 5.38 | 6.44 |
| | 5.82 | 6.11 | 5.71 | 6.48 |
| Mean | 6.10 | 6.24 | 5.54 | 6.27 |
| SD | 0.37 | 0.31 | 0.21 | 0.44 |
| Date | | | | |
| Feb. 27 | 7.44 | 6.58 | 6.3 | 6.88 |
| | 6.44 | 6.28 | 6.45 | 7.19 |
| | 7.24 | 7.4 | 6.47 | 7.32 |
| | 6.55 | 6.66 | 6.24 | 6.4 |
| | 6.72 | 6.79 | 6.24 | 7.08 |
| | 6.84 | 6.86 | 6.76 | 7.37 |
| Mean | 6.87 | 6.76 | 6.41 | 7.04 |
| SD | 0.39 | 0.37 | 0.20 | 0.36 |
| Date | | | | |
| Feb. 28 | 8.06 | 7.31 | 6.84 | 7.30 |
| | 8.20 | 8.10 | 6.91 | 8.12 |
| | 7.60 | 7.65 | 7.23 | 8.35 |
| | 7.70 | 7.17 | 7.10 | 7.85 |
| | 7.55 | 7.16 | 7 | 7 |
| | | 7 | 7.56 | 8.18 |
| Mean | 7.82 | 7.40 | 7.11 | 7.80 |
| SD | 0.29 | 0.41 | 0.26 | 0.54 |
| Date | | | | |
| March 1 | 8.1 | 7.85 | 7.81 | 8.96 |
| | 8.52 | 8.48 | 8.4 | 8.85 |
| | 8.3 | 7.6 | 7.88 | 8.77 |
| | 8.85 | 7.28 | 7.88 | 8.42 |
| | 8 | 8.12 | 8.26 | 8 |
| | | 7.65 | 7.74 | 8.68 |
| Mean | 8.35 | 7.83 | 8.00 | 8.61 |
| SD | 0.34 | 0.42 | 0.27 | 0.35 |
| Date | | | | |
| March 4 | 10.91 | 8.93 | 9.04 | 10.22 |
| | 10.33 | 9.05 | 9.84 | 10.65 |
| | 10.15 | 9.63 | 9.25 | 9.89 |
| | 10.1 | 8.5 | 9.01 | 11.3 |
| | 10.27 | 9.28 | 9.3 | 10.57 |
| | | 9.9 | 9.65 | 10.53 |
| Mean | 10.35 | 9.22 | 9.35 | 10.53 |
| SD | 0.33 | 0.50 | 0.33 | 0.47 |
| Date | | | | |
| March 5 | 10.72 | 9.46 | 9.98 | 11 |
| | 10.26 | 10.24 | 10.84 | 11.4 |
| | 11.18 | 10.4 | 10.6 | 11.32 |
| | 10.58 | 9.58 | 9.85 | 11.2 |
| | 10.6 | 9.38 | 9.67 | 10.74 |
| | | 8.7 | 9.28 | 11.66 |
| Mean | 10.67 | 9.63 | 10.04 | 11.22 |
| SD | 0.33 | 0.62 | 0.58 | 0.32 |
| Date | | | | |
| March 6 | 11.06 | 8.98 | 10.15 | 11.63 |
| | 10.58 | 9.5 | 10.89 | 11.65 |
| | 11 | 10.35 | 10.23 | 11.27 |
| | 10.78 | 10.67 | 9.94 | 10.94 |
| | 10.5 | 9.88 | 10.54 | 11.7 |
| | | 10.22 | 10.75 | 11.95 |
| Mean | 10.78 | 9.88 | 10.35 | 11.44 |
| SD | 0.25 | 0.67 | 0.37 | 0.33 |
| Date | | | | |
| March 7 | 11.27 | 10.05 | 11.8 | 11.75 |
| | 11.33 | 9.2 | 11.47 | 12.28 |
| | 11.37 | 9.84 | 10.88 | 12.48 |
| | 11.74 | 10.64 | 10.55 | 12.54 |
| | 11.72 | 10.04 | 11.15 | 11.56 |
| | | 10.78 | 10.66 | 12.26 |
| Mean | 11.49 | 9.95 | 11.17 | 12.12 |
| SD | 0.23 | 0.52 | 0.49 | 0.44 |
| Date | | | | |
| March 8 | 11.93 | 9.27 | 11.2 | 12.13 |
| | 11.7 | 10.45 | 11.33 | 13.25 |
| | 11.85 | 9.75 | 11.06 | 13.35 |
| | 12.5 | 10.48 | 12 | 12.57 |
| | 11.7 | 11.54 | 11.29 | 12.17 |
| | | 10.9 | 10.94 | 12.84 |
| Mean | 11.94 | 10.30 | 11.38 | 12.69 |
| SD | 0.33 | 0.86 | 0.36 | 0.58 |
| No injections of GPG between 3/8 and 3/15 | | | | |
| Date | | | | |
| March 15 | 20.4 | 16.1 | 18.5 | 19.66 |
| | 19.3 | 15.4 | 15 | 22.5 |
| | 21.2 | 18 | 17.8 | 17.5 |
| | 18.2 | 16.43 | 18.65 | 18.3 |
| | 20.4 | 17 | 17.35 | 21.3 |
| | | 17.85 | 15.74 | 19.25 |
| Mean | 19.90 | 16.59 | 17.46 | 19.85 |
| SD | 1.17 | 0.98 | 1.47 | 2.07 |

EXAMPLE 9

Effects of Gly-Pro-Gly on Human T cells

Gly-Pro-Gly was found to have no effect on normal T cell and B cell functions. The substances have been examined in vitro and in vivo in human and murine systems, respectively. The in vivo experiments are described in Example 11.

The possibility that Gly-Pro-Gly may affect the viability and/or function of normal human circulating lymphomonocytic cells was examined by adding Gly-Pro-Gly to unfractionated and T cell enriched ($CD2^+$=nominal T cells; $CD4^+$ =putative helper/inducer T cell subset; CD8+=putative cytotoxic/suppressor T cell subset) peripheral blood mononuclear cell suspensions from healthy normal blood donors.

T cells were obtained from human blood by first enriching by rosetting with sheep red blood cells according to the method described in Selected Methods in Cellular Immunology, Mishell and Shigi eds., Freeman and Co., San Francisco, pp. 205–207 (1980) followed by centrifugation through a gradient of Ficoll-Paque (Pharmacia, Uppsala, Sweden), according to the methods described by Janossy and Almlot, in Lymphocytes a Practical Approach, Klaus ed., IRL Press, Oxford—Washington DC, pp. 69–70 (1987). Briefly the enriched T cells were resuspended for 5 minutes at 4° C. in Tris-buffered $NH_4Cl$ solution to lyse the red blood cells. The resulting T cell enriched fraction was then further separated into CD4 enriched and CD8 enriched T cells by immunomagnetic cell sorting accord to the methods described by Vartdal et al., Tissue Antigens, 28: 302–312 (1986) and Leivestad et al., Transplant Proc., 19: 265–267 (1987) which are incorporated herein by reference, using monodisperse magnetic beads (DYNABEADS, DYNAL Inc. Oslo Norway) coated respectively with monoclonal antibodies to CD8 and CD4. The DYNABEADS were used according to the manufacturer's instructions for selective depletion of corresponding T cell subsets.

The viability of normal mononuclear cells (MNC) exposed to various concentrations of Gly-Pro-Gly was monitored daily for a period of 4 days by flow cytometry after treatment with propidium iodide according to the method described by Findley et al., Blood, 15;75: 951–957 (1990) which is incorporated herein by reference. These experiments revealed that, even at doses as high as 2 mM and for periods of exposure as long as 4 days, Gly-Pro-Gly did not appreciably affect the viability of cultured monocytes and lymphocytes. Thus, the viability of peripheral blood mononuclear cells exposed to Gly-Pro-Gly (2 mM, 4 days) was 99.67% and that of corresponding unexposed cells was 99.66% (mean of 4 experiments).

EXAMPLE 10

Effect of the peptides on T cell Activity

The in vitro proliferative response of normal T cells was examined after concurrent exposure of unfractionated, and T cell enriched (CD4$^+$ or CD8$^+$ enriched using DYNABEADS M-450 CD4 and DYNABEADS M-450 CD, magnetic beads according to the manufacturer's instructions, DYNAL A. S. Oslo Norway). Vartdal et al. (1986); and Leivestad et al. (1987).

MNC suspensions were exposed to Gly-Pro-Gly and conventional T cell mitogens, in 3 systems including 2 accessory cell systems, the first being monocyte dependent stimulation by either phytohemagglutinin or soluble monoclonal anti-CD3 antibodies, according to the method described by Yamada et al., Eur. J. Immunol., 21: 319–325 (1991) which is incorporated herein by reference, and the second being independent, i.e. stimulated by immobilized solid phase anti-CD3 monoclonal antibodies according to the method described by Van Lier et al., Immunology, 68: 45–50 (1989) which is incorporated herein by reference. The results are indicated as the stimulation index which is calculated as follows: the ratio between radioactive Thymidine incorporated in cell cultures exposed to mitogen alone or mitogen plus Gly-Pro-Gly divided by the radioactive Thymidine incorporated in identical cell cultures exposed to medium alone.

The results of these experiments are summarized in Table 16 and demonstrate that at doses as high as 20 μM, Gly-Pro-Gly exerts marginal if any direct anti-proliferative properties on T cells and does not affect the function of accessory cells (e.g. monocytes and dendritic cells) whose presence is required in two of the above systems.

TABLE 16

| | | STIMULATION INDEX (SI) | | |
|---|---|---|---|---|
| | | | Accessory-cell dependent system | Accessory-cell independent system |
| Cells | Gly—Pro—Gly 20 μM | PHA | Soluble anti-CD3 | Insoluble anti-CD3 |
| PBL | − | 42.6 | 4.6 | 91.8 |
| unfractioned | + | 35.2 | 3.4 | 81.5 |
| CD2 + T-cells + | − | 26.5 | N.D. | N.D. |
| accessory cells | + | 22.8 | N.D. | N.D. |
| − accessory cells | − | N.D. | 0.6 | 407.2 |
| | + | N.D. | 0.4 | 373.4 |
| CD4 + T-cells − | − | N.D. | 1.4 | 527.8 |
| accessory cells | + | N.D. | 1.2 | 490.0 |
| CD8 + T-cells − | − | N.D. | 2.9 | 429.0 |
| accessory cells | + | N.D. | 1.7 | 270.3 |

EXAMPLE 11

Effect of the Peptides on the Humoral Immune Response in Mice

The effects of Gly-Pro-Gly on development of humoral specific antibody responses was examined in mice. For this purpose, Gly-Pro-Gly was administered in adult (4 weeks old, sex matched) Swiss albino outbred mice by intraperitoneal injections given daily for 5 consecutive days. The control group was not given Gly-Pro-Gly, whereas the second and third groups were given 0.5 mg and 5 mg Gly-Pro-Gly respectively.

The pretreated mice were then studied for an antibody response to an unrelated antigen, the hapten trinitrophenol (TNP), the latter having been coupled to different "carrier" molecules whose recognition by murine T cells is not required (lipopolysaccharide (LPS) and Ficoll (Fi)) or is required (ovalbumin (OVA) in order to induce an antibody response. Immediately after administration of the last dose of Gly-Pro-Gly, i.e. on day 5, separate groups of 5 mice were immunized by 2 intraperitoneal injections given 3 weeks apart and consisting of either a T cell dependent antigen, i.e. trinitrophenylated-ovalbumin (OVA-TNP), or T cell independent antigens such as trinitrophenylated lipopolysaccharide (LPS-TNA) and trintrophenylated ficoll (Fi-TNP) according to the method described by Mond et al., J. Immunol., 131: 633–637 (1983) which is incorporated herein by reference. All hapten-carrier conjugates were prepared according to the method described by Eisen, J. Am. Chem. Soc., 75: 4583 (1953) which is incorporated herein by reference. The doses administered to the mice were as follows:

OVA-TNP; 100 μg (protein weight) per injection. Average substitution ratio of OVA-TNP=1:20

LPS-TNP; 25 μg (LPS weight per injection). Average substitution ratio of LPS-TNP=1:5

Ficoll-TNP; 100 μg (Ficoll weight) per injection. Average substitution ratio of Ficoll:TNP=1:30

Serum antibody responses to the TNP group were monitored by the ELISA technique performed on serum samples collected 2 weeks after the second injection. For this purpose, ELISA analyses were performed on each subclass of IgG antibodies, i.e. IgG1, IgG2a, IgG2b and IgG3 and on IgM antibodies.

ELISA assays were performed as follows. Individual wells in Polyvinyl microtiter plates were coated with TNP-conjugated dog albumin according to the method described by Nygren et al., J. Immunol. Met., 85: 87–94 (1985). Serial 2-fold dilutions of individual mouse sera were then added to duplicate wells and incubated. TNP-reactive antibodies were then detected by stepwise addition of enzyme labelled goat antibodies to mouse IgG1, IgG2a, IgG2b, IgG3 or IgM (all obtained from Southern Biotechnology Associates, Birmingham, Ala.) and enzyme substrate. Results are expressed as endpoint titer, the latter being defined as the reciprocal of the highest dilution of serum giving an ELISA absorbance value equal to 3 times that of control wells exposed to buffer alone but not serum.

The results of such analyses are summarized in Table 17 and demonstrate that administration of large doses of Gly-Pro-Gly (5 mg/day/animal for 5 days) do not appreciably influence the humoral immune responsiveness of mice to either T cell dependent (e.g. OVA-TNP) or independent (LPS-TNP or Fi-TNP) antigens compared to mice that have not been pretreated with Gly-Pro-Gly (non-immunized mice in Table 17). Statistical analysis showed that p=0.05 (Wilcoxon's range sum test) when the results obtained from the nonimmunized mice are compared to those obtained from the pretreated mice.

TABLE 17

| | | Immunized mice pretreated with titers ($10^{-2}$) | | | |
|---|---|---|---|---|---|
| Immunogen | Anti-TNP antibody | 0 mg Gly—Pro—Gly | 0.05 mg Gly—Pro—Gly | 5 mg Gly—Pro—Gly | Non-immunized mice |
| OVA-TNP | IgG1 | 1600 (150–5000) | 4500 (2500–5000) | 2770 (200–4000) | 88 (25 . 140) |
| | IgG2a | 280 (40–750) | 800 (250–1500) | 775 (75–2000) | <5 |
| | IgG2b | 190 (20–400) | 1110 (250–1500) | 1000 (40–2000) | <5 |
| | IgG3 | 22 (5–100) | 180 (75–410) | 140 (6–400) | <5 |
| | IgM | 26 (5–100) | 21 (10–40) | 29 (15–50) | <5 |
| Ficoll-TNP | IgG1 | 5 (1–15) | <1 | 3 (1–4) | <1 |
| | IgG2a | 2 (1–5) | <1 | 2 (1–2) | <1 |
| | IgG2b | 1 (1–2) | <1 | 1 (1–2) | <1 |
| | IgG3 | <1 | <1 | <1 | <1 |
| | Igm | 2 (1–4) | 2 (1–3) | 2 (1–4) | <1 |
| LPS-TNP | IgG1 | 130 (10–400) | 240 (5–500) | 170 (50–400) | <1 |
| | IgG2a | 540 (150–1000) | 350 (100–600) | 440 (150–750) | <1 |
| | IgG2b | 125 (75–400) | 180 (30–400) | 260 (100–500) | <1 |
| | IgG3 | 38 (1–150) | 48 (1–150) | 38 (5–130) | <1 |
| | IgM | 15 (5–30) | 32 (5–100) | 18 (10–30) | <1 |

---

What is claimed is:

1. A method of inhibiting human immunodeficiency virus infection of host cells and syncytia formation between infected and non-infected cells, comprising administering to said cells an effective amount of a polypeptide having a C-terminal amide group of the molecular formula:

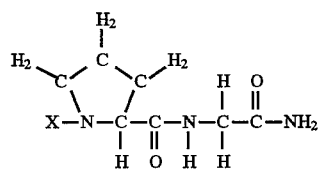

wherein X is selected from the group consisting of hydrogen and about one to four additional amino acid residues.

2. The method according to claim 1 wherein X is selected from the group consisting of glycine, arginyl-glycine and tyrosyl-arginyl-glycine.

3. A composition for inhibiting human immunodeficiency virus infection of host cells and syncytia formation between infected and non-infected cells, comprising an effective amount of a polypeptide having a C-terminal amide group of the molecular formula:

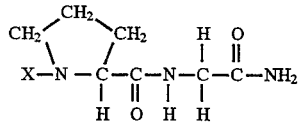

wherein X is selected from the group consisting of hydrogen and about one to four additional amino acid residues.

4. The composition according to claim 3 wherein X is selected from the group consisting of glycine, arginyl-glycine and tyrosyl-arginyl-glycine.

5. The composition according to claim 3 wherein the pharmaceutically acceptable carrier is selected from the group consisting of isotonic saline and isotonic phosphate buffered saline.

6. The method of claim 1, wherein X is glycine.

7. An isolated peptide having the following molecular formula:

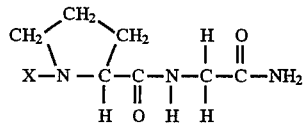

wherein X is selected from the group consisting of glycine, arginyl-glycine, tyrosyl-arginyl-glycine.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 8
        ( B ) TYPE: amino acid
        ( D ) TOPOLOGY: linear ( i i ) MOLECULE TYPE:
        ( A ) DESCRIPTION: peptide ( i x ) FEATURE:
        ( D ) OTHER INFORMATION: sequence is modified with
            t-Boc at amino terminal end. Leu at position 5 is gamma
            leucine.

( x ) PUBLICATION INFORMATION:
        ( A ) AUTHORS: Richards
        ( B ) TITLE: Inhibition of Aspartic Proteinase from
            HIV-2[<]sz;7;0
        ( C ) JOURNAL: FEBS Letters
        ( D ) VOLUME: 253
        ( F ) PAGES: 214-216

( x i ) SEQUENCE DESCRIPTION: SEQ ID NO: 1:

His Pro Phe His Leu Val Ile His
                      5

( 2 ) INFORMATION FOR SEQ ID NO: 2:

( i ) SEQUENCE CHARACTERISTICS:
        ( A ) LENGTH: 5
        ( B ) TYPE: amino acid
        ( D ) TOPOLOGY: linear ( i i ) MOLECULE TYPE:
        ( A ) DESCRIPTION: peptide ( x i ) SEQUENCE DESCRIPTION: SEQ ID NO: 2:

Tyr Arg Gly Pro Gly
           5

( 2 ) INFORMATION FOR SEQ ID NO: 3:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( x i ) SEQUENCE DESCRIPTION: SEQ ID NO: 3:

Gly  Pro  Gly  Arg
              4

( 2 ) INFORMATION FOR SEQ ID NO: 4:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( x i ) SEQUENCE DESCRIPTION: SEQ ID NO: 4:

Arg  Gly  Pro  Gly
              4

( 2 ) INFORMATION FOR SEQ ID NO: 5:

( i ) SEQUENCE CHARACTERISTICS:
    ( A ) LENGTH: 5
    ( B ) TYPE: amino acid
    ( D ) TOPOLOGY: linear ( i i ) MOLECULE TYPE:
    ( A ) DESCRIPTION: peptide ( x i ) SEQUENCE DESCRIPTION: SEQ ID NO: 5:

Arg  Gly  Pro  Gly  Arg
                    5

( 2 ) INFORMATION FOR SEQ ID NO: 6:

( i ) SEQUENCE CHARACTERISTICS:
    ( A ) LENGTH: 4
    ( B ) TYPE: amino acid
    ( D ) TOPOLOGY: linear ( i i ) MOLECULE TYPE:
    ( A ) DESCRIPTION: peptide ( x i ) SEQUENCE DESCRIPTION: SEQ ID NO: 6:

Gly  Pro  Gly  Gly
              4